(12) United States Patent
Flores et al.

(10) Patent No.: US 10,613,484 B2
(45) Date of Patent: *Apr. 7, 2020

(54) INTELLIGENT WAKE-UP ALARM SYSTEM

(71) Applicant: International Business Machines Corporation, Armonk, NY (US)

(72) Inventors: Romelia Flores, Keller, TX (US); Roberto R. Rodriguez, Irving, TX (US); Su Liu, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/545,353

(22) Filed: Aug. 20, 2019

(65) Prior Publication Data

US 2019/0391537 A1 Dec. 26, 2019

Related U.S. Application Data

(63) Continuation of application No. 16/018,228, filed on Jun. 26, 2018.

(51) Int. Cl.
*G04G 13/02* (2006.01)
*A61B 5/024* (2006.01)
(Continued)

(52) U.S. Cl.
CPC ........... *G04G 13/026* (2013.01); *A61B 5/024* (2013.01); *A61B 5/4809* (2013.01); *A61B 5/4812* (2013.01); *G04B 19/24* (2013.01)

(58) Field of Classification Search
CPC combination set(s) only.
See application file for complete search history.

(56) References Cited

U.S. PATENT DOCUMENTS 4,228,806 A 10/1980 Lidow
4,617,525 A 10/1986 Lloyd
(Continued)

FOREIGN PATENT DOCUMENTS

EP 26893011 B1 1/2014

OTHER PUBLICATIONS

"Beddit Sleep Tracker", May 1, 2017, 11 pages, <http://web.archive.org/web/20170501051232/http://www.beddit.com/>.
(Continued)

*Primary Examiner* — Travis R Hunnings
(74) *Attorney, Agent, or Firm* — Joseph P. Curcuru; Stephen R. Yoder

(57) ABSTRACT

In an approach to playing an alarm based on preferred parameters and sleep cycle, identifying a plurality of alarm settings, wherein the plurality of alarm settings includes alarm times; identifying a current time; identifying a range of alarm times from the plurality of alarm settings; in response to determining that individuals are to be monitored for respective sleep statuses based in part on the plurality of alarm settings, identifying the respective sleep statuses, wherein each sleep status comprises one of an awake state and an asleep state; in response to determining at least one respective sleep status is an awake state, determining whether the current time is within the range of alarm times; and in response to determining the first current time is within the range of alarm times, playing an alarm.

20 Claims, 7 Drawing Sheets

(51) Int. Cl.
*A61B 5/00* (2006.01)
*G04B 19/24* (2006.01)

(56) References Cited

U.S. PATENT DOCUMENTS

| | | | |
|---|---|---|---|
| 6,838,994 B2 | 1/2005 | Gutta | |
| 6,928,031 B1 | 8/2005 | Kanevsky | |
| 2012/0300598 A1* | 11/2012 | Murray | G04G 13/02 |
| | | | 368/251 |
| 2013/0252591 A1* | 9/2013 | Sasaki | H04W 4/00 |
| | | | 455/414.1 |
| 2016/0073951 A1 | 3/2016 | Kahn | |
| 2016/0187856 A1 | 6/2016 | Vilermo | |
| 2016/0217672 A1 | 7/2016 | Yoon | |
| 2016/0234034 A1 | 8/2016 | Mahar | |
| 2017/0087330 A1 | 3/2017 | Kahn | |

OTHER PUBLICATIONS

Flores et al., "Intelligent Wake-Up Alarm System", U.S. Appl. No. 16/018,228, filed Jun. 26, 2018, 57 pages.
Henry, Alan, "Five Best Sleep Tracking Gadgets or Apps" lifehacker, Mar. 31, 2013 11:00am, 125 pages, <https:// lifehacker.com/5993005/five-best-sleep-tracking-gadgets-or-apps>.

* cited by examiner

INTELLIGENT WAKE-UP ALARM SYSTEM

BACKGROUND

The present invention relates generally to the field of alarm systems and, more particularly, to alarm systems utilizing a collection of parameter services information and sleep tracking information.

The sleep cycle is an oscillation between the rapid eye movement (REM) and non-REM stages of sleep. The standard figure given for the average length of the sleep cycle is 90 minutes for an adult. A 7-8-hour sleep typically includes five cycles, the middle two of which tend to be longer. REM takes up more of the cycle as the night goes on. There are several stages of non-REM sleep. N1 (non-REM stage 1) is when the person is drowsy or falling asleep. Brain waves and muscle activity start to decrease at this stage. N2 is when the person experiences light sleep. Eye movement has stopped by this time. Brain wave frequency and muscle tone are decreased. The heart rate and body temperature go down. N3 and N4 are the more difficult stages to be awakened from. Breathing, blood pressure and body temperature are reduced. N3 and N4 are often referred to as "deep sleep." The REM stage is distinguished by random/rapid movement of the eyes, accompanied with low muscle tone throughout the body, and the propensity of the sleeper to dream vividly. The REM stage is the deepest stage of sleep.

An alarm clock is a clock designed to alert an individual or group of individuals at specified time. The primary function of these clocks is to awaken people from their night's sleep or short naps; they are sometimes used for other reminders as well. Most alarm clocks use sound to awake individuals, while others use light or vibrations.

SUMMARY

The present invention can be embodied as a method, a computer program product, and/or a computer system, as described herein. Aspects of the present invention comprise: identifying a first range of alarm times to play a first alarm in a set of alarm settings, monitoring a user for a sleep status, determining the sleep status to be an awake status at a first time, determining whether the first time is within the first range of alarm times, and responsive to determining the first time is within the first range of alarm times, playing the first alarm.

DETAILED DESCRIPTION

Figure 1:
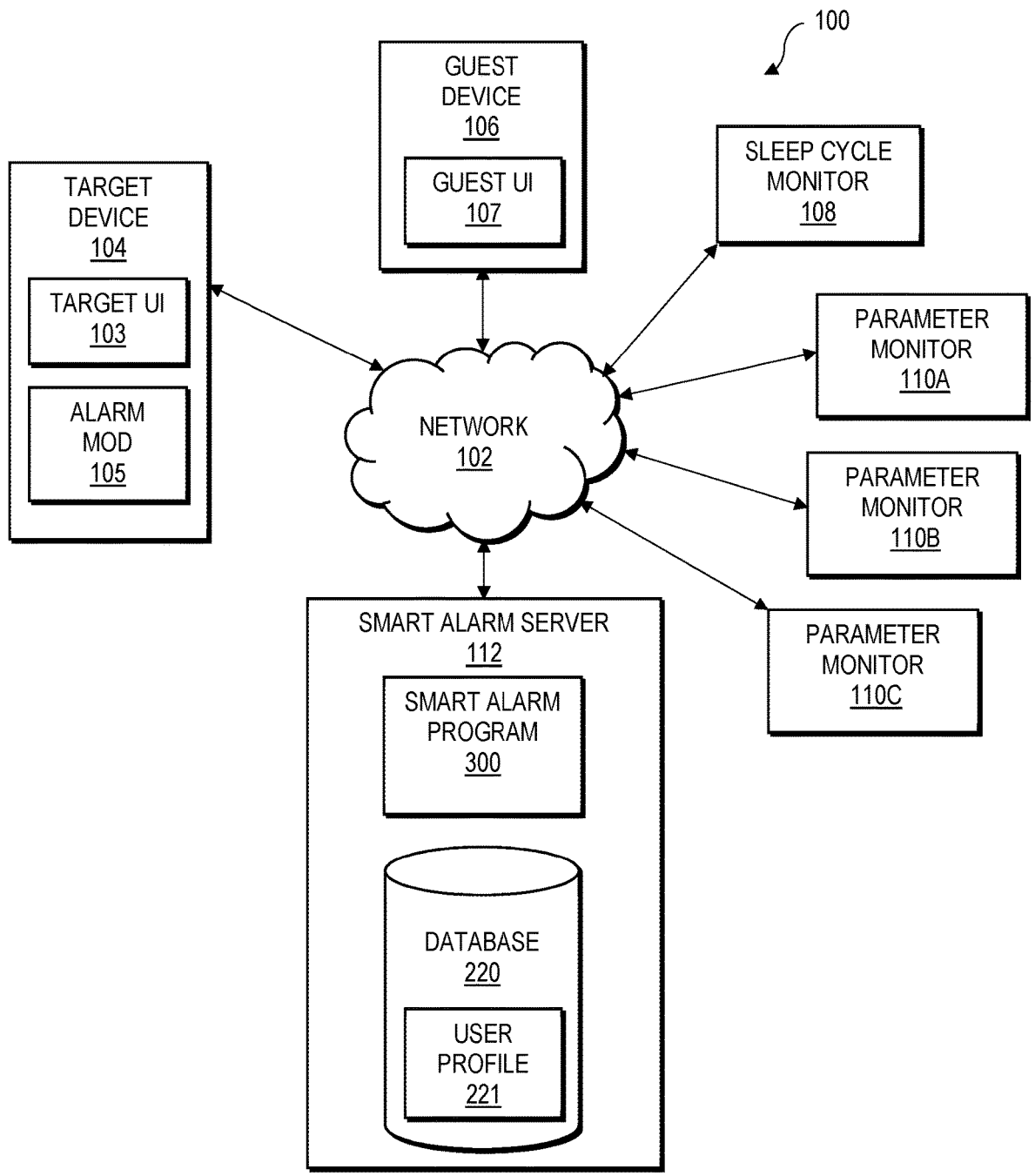
FIG. 1 is a functional block diagram illustrating a computing environment for playing an alarm based on a user's preferred parameters and sleep cycle, in accordance with a first embodiment of the present invention.

Embodiments of the present invention recognize in some situations, an individual's waking and sleeping habits vary day-to-day based on specific conditions such as meetings, weather conditions, etc. An individual may set an alarm for a variety of reasons, such as to wake up the individual in the morning before travelling to work. However, circumstances, such as inclement weather or heavy traffic, may lengthen the amount of travel time for the individual. For example, a worker typically needs 15 minutes to travel to his workplace. The worker sets an alarm in the morning, considering the 15 minutes needed to arrive to work on time. However, snow fall the night before lengthens the travel time to the workplace from 15 minutes to 30 minutes. The worker, awakened by his previously set alarm, would likely be late to work since the alarm time did not consider the delay in travel time due to the weather. In some cases, an individual may want to wake up immediately if an event occurs. For example, an individual with guests staying over would like to be awake when the individual's guests are awake in order to be hospitable. A standard alarm clock would wake up the individual only at the designated time. Additionally, it is known that physical changes occur as people get older. One change is the sleep patterns of aging people. As people age, they have a harder time falling asleep (sleep latency) and staying asleep, which may lead to sleep problems. Sleep patterns are classified on a spectrum from light sleep to deep sleep with occasional periods of REM sleep. It is typical for a sleep cycle to repeat several times throughout the night. Snoring, insomnia, and medications all have an impact on sleep patterns.

Embodiments of the present invention provide a method to alert a user based on the user's sleep cycle information as well as information from external sources. External sources may be variables that affect an individual's wake up time. In some embodiments, for example, external sources include weather, calendar, traffic, and household sleep tracking information. Parameters from these sources are monitored and, in the event of a change in parameters that could affect an individual's wake up time, the alarm time is adjusted. For example, road construction on a major highway likely affects the traffic that travels on the major highway. A parameter monitor may monitor the traffic information for the major highway. In this example, a worker will be travelling to work on the major highway while the road construction is ongoing. In some embodiments, the worker's alarm device utilizes the traffic information for the major highway to adjust the worker's alarm time to account for the longer travel time due to the road construction. In this example, the worker's alarm device constantly monitors external sources, such as traffic information, and adjusts the alarm time if needed until it is time for the alarm. In some embodiments, an individual's sleep cycle may be monitored to determine the best times to wake up an individual during the individual's sleep. Some modern alarm clocks have sensors to identify when a person is in a light stage of sleep. Awaking someone who is deeply asleep causes tiredness, even if the person has had adequate sleep. Waking up during deep sleep causes grogginess or disorientation. Waking up during the early stages of sleep, or "light sleep" tends to make people feel energetic and alert upon awakening. Furthermore, in some embodiments, an individual's sleep cycle information may be prioritized above or below information received from external sources. An individual may prioritize waking up during light sleep over waking up on an adjusted time due to a parameter change from an external source. In the above road construction example, the worker prioritizes waking up during light sleep. The worker's alarm device adjusts the wake-up time to a period of time when the worker is undergoing light sleep. The alarm time may be adjusted to a time after the previously adjusted alarm time since the worker prioritizes waking up during light sleep or the alarm time may be adjusted to a time before the previously adjusted alarm time. Conversely, an individual may prioritize waking up during light sleep below waking up on an adjusted time due to a parameter change from an external source. In this case, the alarm device allows individuals to wake up during deep sleep if the previously adjusted time falls within a period of deep sleep.

Embodiments of the present invention will now be described in detail with reference to the Figures. It is to be understood that these embodiments are described only for the purpose of illustration and help those skilled in the art to understand and implement the present invention, without suggesting any limitation as to the scope of the invention. The invention described herein can be implemented in various manners other than the ones explicitly described herein.

FIG. 1 is a functional block diagram illustrating a computing environment for playing an alarm based on a user's preferred parameters and sleep cycle, in accordance with an embodiment of the present invention. For example, FIG. 1 is a functional block diagram illustrating computing environment 100. Computing environment 100 includes target device 104, guest device 106, sleep cycle monitor 108, parameter monitors 110A, parameter monitor 110B, parameter monitor 110C, and smart alarm server 112 connected over network 102. Target device 104 includes target user interface (target UI) 103 and alarm mod 105. Guest device 106 includes guest user interface (guest UI) 107. Smart alarm server 112 includes smart alarm program 300 and database 220. Database 220 includes user profile 221.

In various embodiments, smart alarm server 112 is a computing device that can be a standalone device, a server, a laptop computer, a tablet computer, a netbook computer, a personal computer (PC), or a desktop computer. In another embodiment, smart alarm server 112 represents a computing system utilizing clustered computers and components to act as a single pool of seamless resources. In general, smart alarm server 112 can be any computing device or a combination of devices with access to some or all of target device 104, guest device 106, sleep cycle monitor 108, and parameter monitors 110A, 110B, and 110C, and with access to and/or capable of executing smart alarm program 300. Smart alarm server 112 may include internal and external hardware components, as depicted/described in further detail with respect to FIG. 5.

In this embodiment, smart alarm program 300 is stored on smart alarm server 112. In other embodiments, smart alarm program 300 may reside on another computing device (e.g., target device 104), provided it can access and/or receive data from some or all of target device 104, guest device 106, sleep cycle monitor 108, and parameter monitors 110A, 110B, and 110C. In yet other embodiments, smart alarm program 300 may be stored externally and accessed through a communication network, such as network 102. Operations executed by smart alarm program 300 are discussed in greater detail with respect to FIGS. 3A-3C and 4.

In general, smart alarm program 300 operates to play an alarm for a user based on data collected from parameter services and/or data regarding a user's sleep cycle. One or more users of smart alarm program 300 uses a smart device, such as target device 104, to select alarm settings and sleep cycle priorities for the user. In various embodiments, alarm settings are one or more set alarm times and/or ranges of alarm times and sleep cycle prioritization are rules to decide if sleep cycle information should be utilized with respect to alarm settings. Smart alarm program 300 obtains the current time and identifies the set alarm based on a user's alarm settings. Having identified the set alarm, smart alarm program 300 can determine whether guest(s) are present. Smart alarm program 300 identifies the guests and the sleep status of the guests from information collected by a parameter monitor, such as parameter monitor 110A, specific to tracking household sleep patterns. The parameter monitor may obtain sleep pattern information from wearable devices or wearable personal sleep trackers and smart alarm program 300 determines whether the guests are awake or asleep. Based on the awakeness of the guests, smart alarm program plays an alarm for the user if the guests are awake during a designated time period. Otherwise, smart alarm program 300 returns to obtain the current time in another iteration of smart alarm program 300.

If no guests are present, smart alarm program 300 determines whether the user has scheduled calendar events. In some embodiments, a parameter monitor, such as parameter monitor 110B, specific to tracking calendar events, is used by smart alarm program 300 to determine whether scheduled calendar events exist for the day of the set alarm time. If scheduled calendar events exist, smart alarm program 300 identifies an event and the time of the event. If smart alarm program 300 determines an event is near the set alarm time and within a certain amount of time from the set alarm time, smart alarm program 300 determines whether there is a cancellation of the event.

If smart alarm program 300 determines a user does not have scheduled calendar events, smart alarm program 300 identifies the current weather conditions. In some embodiments, a parameter monitor, such as parameter monitor 110C, specific to tracking weather events, is used by smart alarm program 300 to identify the current weather conditions. In some embodiments, smart alarm program 300 determines whether there are unsafe travel conditions from weather-related data. In other embodiments, a parameter monitor, specific to tracking traffic events, is used by smart alarm program 300 to identify unsafe traffic conditions. If smart alarm program 300 determines there is a cancellation of an event or if smart alarm program 300 determines there are unsafe travel conditions, smart alarm program 300 proceeds to cancel the set alarm time and update the alarm settings to replace the set alarm time with a backup alarm time.

If smart alarm program 300 determines there are safe travel conditions, smart alarm program 300 determines whether the user's sleep cycle is prioritized. Smart alarm program 300 identifies the point in the user's sleep cycle. In some embodiments, a sleep cycle monitor, such as sleep cycle monitor 108, is used by smart alarm program 300 to monitor sleep patterns and determine the sleep cycle point of the user. Smart alarm program 300 determines whether the sleep cycle point is an appropriate period for waking the user. If smart alarm program 300 determines the sleep cycle point is not an appropriate period for waking the user, smart alarm program 300 proceeds to cancel the set alarm time and updates the alarm settings to replace the set alarm time with a backup alarm time. If smart alarm program 300 determines the sleep cycle point is an appropriate period for waking the user, smart alarm program 300 proceeds to play an alarm for the user.

Network 102 can be, for example, a local area network (LAN), a wide area network (WAN) such as the Internet, or a combination of the two, and may include wired, wireless, fiber optic or any other connection known in the art. In general, network 102 can be any combination of connections and protocols that will support communications between smart alarm server 112, target device 104, guest device 106, sleep cycle monitor 108, and parameter monitors 110A, 110B, and 110C, in accordance with a desired embodiment of the present invention.

Database 220 is a data repository that may be written to and read by smart alarm program 300. Parameter and sleep cycle priorities, alarm settings, guest information, user sleep cycle information collected by a sleep cycle monitoring device (e.g. sleep cycle monitor 108), and information from parameter sources collected from parameter information monitors (e.g. parameter monitors 110A, 110B, and 110C) may be stored to database 220. In some embodiments, database 220 may be written to and read by programs and entities outside of computing environment 100 in order to populate the repository with parameter and sleep cycle priorities, alarm settings, guest/user sleep cycle information, and parameter sources information.

Database 220 includes a user profile, user profile 221, which can be accessed on database 220 by a user of target device 104 to build a user profile. The user profile includes user sleep cycle information, parameter and sleep cycle priorities, and alarm settings. A user of target device 104 may link sleep cycle monitoring devices, such as sleep cycle monitor 108, and parameter information monitors, such as parameter monitors 110A, 110B, and 110C, to user profile 221. The user of target device 104 may also input user-specific parameter and sleep cycle priorities and alarm settings. User profile 221 may be updated by the user of target device 104 or any relevant third party by a computing device, such as a teacher, a parent or guardian, a family member or friend of the user, or an employer of the user.

In various embodiments, target device 104 is a computing device that can be a standalone device, a server, a laptop computer, a tablet computer, a netbook computer, a personal computer (PC), a desktop computer, a personal digital assistant (PDA), a smart phone, a smart alarm clock, or any programmable electronic device capable of communicating with smart alarm server 112 via network 102. In another embodiment, target device 104 represents a computing system utilizing clustered computers and components to act as a single pool of seamless resources. In general, target device 104 can be any computing device or a combination of devices with access to smart alarm server 112, and with access to and/or capable of executing smart alarm program 300. In some embodiments, target device 104 can communicate directly or indirectly with guest device 106. Target device 104 may include internal and external hardware components, as depicted/described in further detail with respect to FIG. 5.

Target device 104 includes a user interface (UI), target UI 103, which executes locally on target device 104 and operates to provide a UI to a user of target device 104. Target UI 103 further operates to receive user input from a user via the provided user interface, thereby enabling the user to interact with target device 104. In one embodiment, target UI 103 provides a user interface enabling a user of target device 104 to interact with smart alarm program 300 of smart alarm server 112 via network 102. In various examples, the user interacts with smart alarm program 300 in order to submit alarm settings, submit parameter and sleep cycle priorities, submit guest information, view sleep cycle information, view parameter changes, and receive alarms. In one embodiment, target UI 103 is stored on target device 104. In other embodiments, target UI 103 is stored on another computing device (e.g., smart alarm server 112), provided target UI 103 can access and is accessible by target device 104 and smart alarm program 300.

Target device 104 includes an alarm module, alarm mod 105, which executes locally on target device 104 and operates to provide a module to play alarms for a user. In some embodiments, alarm mod 105 is a speaker that can play customizable sounds or music as an alarm. In other embodiments, alarm mod 105 uses vibration functionality of target device 104 and/or displays lights as an alarm. In one embodiment, alarm mod 105 is stored on target device 104. In other embodiments, alarm mod 105 is stored on another computing device (e.g., smart alarm server 112), provided alarm mod 105 can access and is accessible by target device 104 and smart alarm program 300.

Guest device 106 is a computing device, in some embodiments similar to target device 104, capable of communicating with smart alarm server 112 via network 102. In another embodiment, guest device 106 represents a computing system utilizing clustered computers and components to act as a single pool of seamless resources. In general, guest device 106 can be any computing device or a combination of devices with access to smart alarm server 112, and with access to and/or capable of executing smart alarm program 300. In one embodiment, a plurality of guest devices exists, where each guest device belongs to a guest submitting information to a target device (e.g., target device 104) by smart alarm program 300. In some embodiments, guest device 106 can communicate directly or indirectly with target device 104. Guest device 106 may include internal and external hardware components, as depicted/described in further detail with respect to FIG. 5.

Guest device 106 includes a user interface (UI), guest UI 107, which executes locally on guest device 106 and operates to provide a UI to a user of guest device 106. Guest UI 107 further operates to receive interaction from a user via the provided user interface, thereby enabling the user to interact with guest device 106. In one embodiment, guest UI 107 provides a user interface enabling a user of guest device 106 to interact with smart alarm program 300 of smart alarm server 112 via network 102. In various examples, the user interacts with smart alarm program 300 in order to submit guest information. In one embodiment, guest UI 107 is stored on guest device 106. In other embodiments, guest UI 107 is stored on another computing device (e.g., smart alarm server 112), provided guest UI 107 can access and is accessible by at least guest device 106 and smart alarm program 300. In general, computing environment 100 can included any number of guest devices 106 that can interface with smart alarm program 300, as described herein, without departing from the scope of the invention.

In general, sleep cycle monitor 108 is a device that can monitor sleep patterns and help predict future sleep patterns in association with a computing device, in some embodiments similar to target device 104. In some embodiments, sleep cycle monitor 108 is one or more wearable devices that can be utilized for polysomnography (PSG), or the study of sleep, while monitoring an individual's movement and activity while the individual is asleep. PSG is a comprehensive recording of the biophysiological changes that occur during sleep. PSG monitors many body functions, including brainwaves, eye movements, heart rate, muscle activity or skeletal muscle activation, oxygen levels, breathing/air flow, and volume and frequency of snoring activity during sleep. In other embodiments, sleep cycle monitor 108 is a wearable personal sleep tracker capable of monitoring a range of inputs such as physical activity, direction, location, sound, skin conductivity, and heart rate, using accelerometers, optical sensors, bioelectric impedance sensors, ballistocardiography, and/or radio wave technology. The human body responds differently at each stage of sleep. Information gathered from sleep cycle monitor 108 used while an individual is asleep can be used to distinguish the different stages of sleep. For example, a sleep cycle monitor collects physical information from personal sleep tracking devices on an asleep user. From the physical information collected by the sleep cycle monitor and the personal sleep tracking devices, smart alarm program 300 can determine, for example, that the user is experiencing non-REM stage 3 sleep, which is associated with deep sleep. In some embodiments, sleep cycle monitor 108 is capable of communicating with smart alarm server 112 via network 102. Sleep cycle monitor 108 may also be used in association with target device 104 and/or guest device 106. In general, computing environment 100 can included any number of sleep cycle monitors 108 that can interface with smart alarm program 300, as described herein, without departing from the scope of the invention.

In general, parameter monitors 110A, 110B, and 110C (collectively, parameter monitors 110) are devices that can send and receive information from an external parameter data source in association with a computing device, in some embodiments similar to target device 104. In other embodiments, parameter monitors 110 are web services that periodically, or as necessary, report data or software modules of smart alarm program 300 that periodically query or interface with various services to obtain the data. An external parameter data source is an external system that collects data based on user preferences for alarm settings. An external parameter data source may be user-inputted or collected from various sensors, instruments, devices, or databases. In some embodiments, parameter monitors 110 consist of multiple devices that obtain appropriate data from multiple external parameter data sources. A user of target device 104 may link one or more external parameter data sources with parameter monitors 110 in order for parameter monitors 110 to utilize the data received from the external parameter data sources. For example, a user of target device 104 who is interested in possible weather-related travel delays links a weather data system from the user's location with parameter monitor 110A. Parameter monitors 110 receive data from external parameter data sources and monitors the data, based on user configured preferences, for any significant changes in data that affect an alarm time. If parameter monitors 110 recognize a significant change in data, smart alarm program 300 calculates the amount of time the alarm time must adjust to. In the above example, parameter monitor 110A collects weather-related data and monitors the data for weather precipitation patterns and the user of target device 104 configures weather precipitation patterns, such as snow, sleet, ice, and rain, as significant changes in weather data. In general, computing environment 100 can included any number of parameter monitors 110 that can interface with smart alarm program 300, as described herein, without departing from the scope of the invention.

Figure 2:
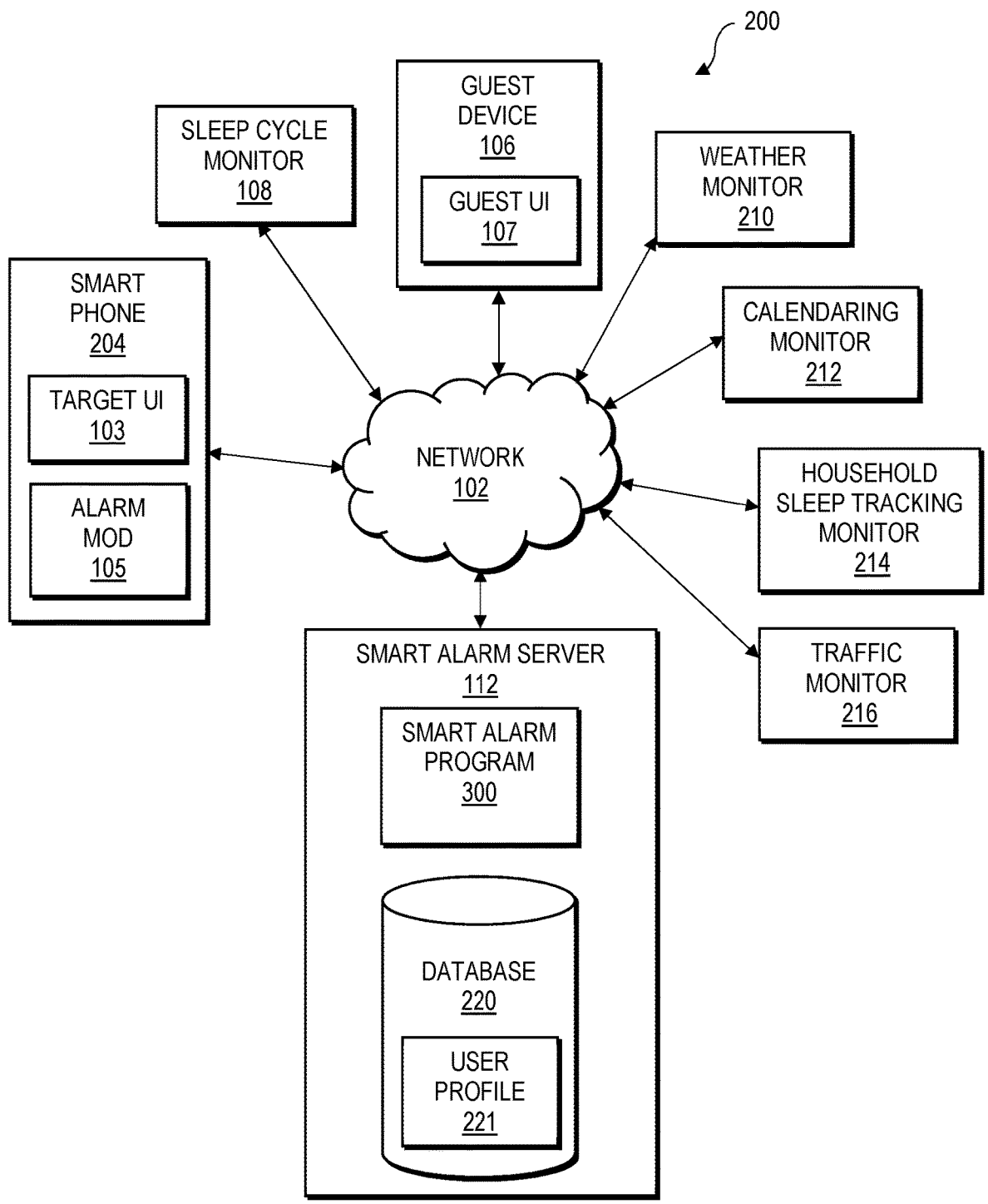
FIG. 2 is a functional block diagram illustrating a computing environment for playing an alarm based on a user's preferred parameters and sleep cycle, in accordance with a second embodiment of the present invention.

FIG. 2 is a functional block diagram illustrating a computing environment for playing an alarm based on a user's preferred parameters and sleep cycle, in accordance with an embodiment of the present invention. For example, FIG. 2 is a functional block diagram illustrating computing environment 200. Computing environment 200 includes smart phone 204, guest device 106, sleep cycle monitor 108, weather monitor 210, calendaring monitor 212, household sleep tracking monitor 214, traffic monitor 216, and smart alarm server 112 connected over network 102. Smart phone 204 includes target UI 103 and alarm mod 105. Guest device 106 includes guest UI 107.

In the specific embodiment depicted in FIG. 2, target device 104 is represented by smart phone 204. As described above with respect to target device 104, smart phone 204 operates as a handheld personal device with a mobile operating system and an integrated mobile broadband cellular network connection for voice, SMS, Internet data, and Wi-Fi communication, capable of communicating with smart alarm server 112 via network 102 and with access to and/or capable of executing smart alarm program 300. Smart phone 204 may include internal and external hardware components, as depicted/described in further detail with respect to FIG. 5. Smart phone 204 has built-in alarm clock functionalities. In various examples, a user of smart phone 204 interacts with smart alarm program 300 in order to in order to submit alarm settings, submit parameter and sleep cycle priorities, submit guest information, view sleep cycle information, view parameter changes, and receive alarms.

Weather monitor 210 is a device that can send and receive information from an external weather data source in association with a computing device, such as smart phone 204. In some embodiments, weather monitor 210 obtains weather-related data from multiple weather data sources and monitors the data for significant changes. Weather data sources may be personal or commercial weather stations. A user of smart phone 204 may link weather stations relevant to the user's location, the user's travel destination, and the user's desired travel route. Weather-related data includes forecast parameters such as temperature, cloud coverage, humidity, chance of precipitation, dew point, and pressure. Weather monitor 210 may also receive weather-related cancellation information. Many local weather stations list closings and delays for schools, community events, and buildings. A user of smart phone 204 may configure weather monitor 210 to monitor weather-related data at certain intervals (i.e. constantly, every 15 minutes, hourly, etc.) and may configure what constitutes a significant weather change. For example, a user may configure any weather-related event that changes a travel time as a significant weather change. Significant weather changes may include snowfall, heavy rain, or tornadoes, as these weather events typically alter travel time. In other embodiments, weather monitor 210 is a web service that periodically, or as necessary, report weather-related data or software modules of smart alarm program 300 that periodically query or interface with various services to obtain the weather-related data. In general, computing environment 200 can included any number of weather monitors 210 that can interface with smart alarm program 300, as described herein, without departing from the scope of the invention.

Calendaring monitor 212 is a device that can send and receive information from an external calendar data source in association with a computing device, such as smart phone 204. In some embodiments, calendaring monitor 212 obtains schedule and calendar-related data of a user of smart phone 204 from multiple calendar data sources and monitors the data for significant changes. Calendar data sources may include social media calendars, business calendars, community event calendars, or user-inputted calendars. Calendar-related data may include business meetings, family events, community events, and/or personal/leisure activities. Calendaring monitor 212 may also receive notices of meeting cancellations, delays, and reschedules. A user of smart phone 204 may configure calendaring monitor 212 to monitor calendar-related data at certain intervals (i.e. constantly, every 15 minutes, hourly, etc.) and may configure what constitutes a significant calendar change. For example, a user may configure any calendar-related event that changes a travel time as a significant calendar change. Significant calendar changes may include cancellations or delays, as these calendar events typically alter times when a user would or would not travel. In general, computing environment 200 can included any number of calendaring monitors 212 that can interface with smart alarm program 300, as described herein, without departing from the scope of the invention.

Household sleep tracking monitor 214 is a device that can send and receive information from an external household sleep tracking data source in association with a computing device, such as smart phone 204. In some embodiments, household sleep tracking monitor 214 obtains household sleep tracking data from a guest device, such as guest device 106. In some embodiments, guest device 106 are one or more sleep cycle monitor devices that can monitor sleep patterns for members of a household or visitors of a household. As described with respect to sleep cycle monitor 108, sleep pattern information can be obtained from wearable PSG devices or wearable personal sleep trackers. Examples of sleep pattern information of members of a household or visitors of a household include information related to whether the guest is asleep or awake. A user of smart phone 204 may configure household sleep tracking monitor 214 to notify the user via smart phone 204 of when a member of a household or visitor of a household is awake. For example, a user who desires to be awake when a visitor of the household is awake, may configure household sleep tracking monitor 214 to send information to smart phone 204 whenever the visitor's sleep pattern changes from asleep to awake. In this case, smart phone 204 would immediately play an alarm for the user to wake up immediately. In some embodiments, household sleep tracking monitor 214 can be configured to send sleep pattern information, like how long the member of a household or visitor of a household is awake, to smart phone 204 only during particular times of day. For example, a user of smart phone 204 may configure household sleep tracking monitor 214 to only send information when the sleep pattern of a visitor changes from asleep to awake after 7:00 a.m. and the visitor remains awake for 10 minutes. In general, computing environment 200 can included any number of household sleep tracking monitors 214 that can interface with smart alarm program 300, as described herein, without departing from the scope of the invention.

Traffic monitor 216 is a device that can send and receive information from an external traffic data source in association with a computing device, such as smart phone 204. In some embodiments, traffic monitor 216 obtains traffic-related data of a travel route of a user of smart phone 204 from multiple traffic data sources and monitors the data for significant changes. Traffic data sources may include historical traffic data, real-time live traffic feeds, and predictive traffic models. Historical traffic data is used with the idea that travel speeds follow a week-long pattern. For example, at 8:00 a.m. on Monday of one week, the travel speeds of a given road segment are expected to be similar to those at 8:00 a.m. on Monday of another week. However, congestion and travel speeds may differ significantly for the same road segment, at the same time of day, but on different days of the week. For example, travel speeds on the given road segment at 8:00 a.m., Sunday, could be much faster than at 8:00 a.m., Monday. Live traffic feeds provide current travel speeds using a number of sources, such as GPS receivers in vehicles and speed sensors on roads. Predictive traffic models utilize algorithms in conjunction with historical traffic data and live traffic feeds to predict future travel speeds. A user of smart phone 204 may link traffic data sources relevant to the user's location, the user's travel destination, and the user's desired travel route. Traffic monitor 216 may also receive notices of traffic jams, road construction, and car accidents. A user of smart phone 204 may configure traffic monitor 216 to monitor traffic-related data at certain intervals (i.e. constantly, every 15 minutes, hourly, etc.) and may configure what constitutes a significant traffic change. For example, a user may configure any traffic-related event that changes a travel time or requires a rerouting of a travel route as a significant traffic change. Significant traffic changes may include road construction or car accidents, as these traffic events typically alter travel time. In some embodiments, travel advisory alerts issued by weather and news services may also be collected by traffic monitor 216 to identify unsafe traffic conditions. Alerts may include heavy traffic, heavy road construction, or traffic collisions. In other embodiments, data collected from multiple sources (such as from a weather monitor and a traffic monitor) may be used together in determinations for whether there are unsafe travel conditions. In general, computing environment 200 can included any number of traffic monitors 216 that can interface with smart alarm program 300, as described herein, without departing from the scope of the invention.

To illustrate the functionality described above with respect to FIG. 2, in one specific example, a user of smart phone 204, Abel, inputs alarm settings and sleep cycle priorities into smart phone 204 using target UI 103. Abel's alarm settings and sleep cycle priorities are stored on database 220 as a user profile (user profile 221). Abel has a guest staying at Abel's house. Abel would like to be awoken if the guest is awake between 7:00 a.m. and 9:00 a.m. Alternatively, Abel would like to be awoken at 9:00 a.m. if the guest has not awoken by then. Abel inputs an alarm time for 9:00 a.m. and sets a range of 7:00 a.m. to 9:00 a.m. to play in the event the guest wakes up during those times. Smart alarm program 300 obtains the current time and identifies the set alarm time for 9:00 a.m. Smart alarm program 300 determines a guest is present since the guest's personal device, guest device 106 communicates over network 102 with smart phone 204 via Bluetooth communication and identifies the guest. Guest device 106 is a personal sleep tracking device. Household sleep tracking monitor 214 obtains the sleep tracking data from guest device 106 to monitor whether the guest is asleep or awake. In a scenario, the guest is awake. The sleep tracking data obtained by household sleep tracking monitor 214 is representative of a person who is awake. Smart alarm program 300 determines the guest is awake. Smart alarm program 300 determines if the current time is within the alarm settings set by Abel. In one scenario, the current time is 6:30 a.m. Smart alarm program 300 determines the current time is not within alarm settings and returns to obtain the current time at a later interval. In another scenario, the current time is 7:30 a.m. Smart alarm program 300 determines the current time is within alarm settings. Smart alarm program 300 proceeds to play an alarm for Abel at 7:30 a.m. using alarm mod 105 on smart phone 204. In another scenario, the guest remains asleep. The sleep tracking data obtained by household sleep tracking monitor 214 is representative of a person who is asleep. Smart alarm program 300 determines the guest is asleep. Smart alarm program 300 determines if the current time is of or after the set alarm time. In one scenario, the current time is 8:30 a.m. Smart alarm program 300 determines the time is not of or after the alarm time and so, returns to obtain the current time at a later interval. In another scenario, the current time is 9:00 a.m. Smart alarm program 300 determines the current time meets the alarm time. Smart alarm program 300 proceeds to play an alarm for Abel at 9:00 a.m. using alarm mod 105 on smart phone 204.

In another specific example to illustrate the functionality described above with respect to FIG. 2, a user of smart phone 204, Abel, inputs alarm settings and sleep cycle priorities into smart phone 204 using target UI 103. Abel's alarm settings and sleep cycle priorities are stored on database 220 as a user profile (user profile 221). Abel would like to be awoken at 8:00 a.m. Alternatively, if Abel's morning business meeting is cancelled, Abel would like to be awoken at 9:30 a.m. Abel inputs an alarm time for 8:00 a.m. and a backup alarm at 9:30 a.m. to play in the event the morning business meeting is cancelled. Smart alarm program 300 obtains the current time. Smart alarm program 300 identifies the set alarm time for 8:00 a.m. Smart alarm program 300 determines a guest is not present since no guest device is found by household sleep tracking monitor 214. Smart alarm program 300 proceeds to determine whether Abel has scheduled calendar events. Abel has linked his work meeting calendar with calendaring monitor 212. Calendaring monitor 212 is used by smart alarm program 300 to determine whether scheduled calendar events exist for the day of the set alarm time. Calendaring monitor 212, obtains schedule and calendar-related data of Abel from multiple calendar data sources, including his work meeting calendar. Smart alarm program determines there are scheduled calendar events. Smart alarm program 300 identifies the morning business meeting and the time of the morning business meeting using information collected by calendaring monitor 212. Smart alarm program 300 determines whether the morning business meeting is within a certain amount of time from the set alarm time (8:00 a.m.). Abel configures smart alarm program to consider events to be near an alarm time if they are within 2 hours of the alarm time. Smart alarm program 300 determines the morning business meeting is near the set alarm time. Smart alarm program 300 determines whether there is a cancellation of the morning business meeting. Calendaring monitor 212 receives notices of meeting cancellations, delays, and reschedules. Calendaring monitor 212 receives information that the morning business meeting was cancelled. Smart alarm program 300 cancels the set alarm (8:00 a.m.) and updates the alarm settings so that the backup alarm (9:30 a.m.) is the set alarm. Smart alarm program 300 determines if the current time is of or after the set alarm time. In one scenario, the current time is 7:00 a.m. Smart alarm program 300 determines the time is not of or after the alarm time and so, returns to obtain the current time at a later interval. In another scenario, the current time is 9:30 a.m. Smart alarm program 300 determines the current time meets the alarm time. Smart alarm program 300 proceeds to play an alarm for Abel at 9:30 a.m. using alarm mod 105 on smart phone 204.

In another specific example to illustrate the functionality described above with respect to FIG. 2, a user of smart phone 204, Abel, inputs alarm settings and sleep cycle priorities into smart phone 204 using target UI 103. Abel's alarm settings and sleep cycle priorities are stored on database 220 as a user profile (user profile 221). Abel would like to be awoken at 8:00 a.m. Alternatively, if the weather results in unsafe travel conditions to his workplace, Abel would like to be awoken at 9:30 a.m. Abel inputs an alarm time for 8:00 a.m. and a backup alarm at 9:30 a.m. to play in the event of inclement weather. Smart alarm program 300 obtains the current time. Smart alarm program 300 identifies the set alarm time for 8:00 a.m. Smart alarm program 300 determines a guest is not present since no guest device is found by household sleep tracking monitor 214. Smart alarm program 300 proceeds to determine whether Abel has scheduled calendar events. Abel has no scheduled calendar events. Smart alarm program 300 determines no scheduled calendar events exist. Weather monitor 210 is used by smart alarm program 300 to identify the current weather conditions. Weather monitor 210 obtains weather-related data from multiple weather data sources and monitors the data. Abel links weather stations relevant to the Abel's location, the Abel's workplace location, and the Abel's desired travel route with smart alarm program 300 via target UI 103 on smart phone 204. Smart alarm program 300 uses weather monitor 210 to identify whether there are unsafe travel conditions. Alternatively, smart alarm program 300 uses traffic monitor 216 to identify unsafe traffic conditions. Unsafe traffic conditions are typical of unsafe travel conditions. Traffic monitor 216 obtains traffic-related data from multiple traffic data sources. Smart alarm program 300 determines there is unsafe travel conditions from data received from weather monitor 210 and traffic monitor 216. Smart alarm program 300 cancels the set alarm (8:00 a.m.) and updates the alarm settings so that the backup alarm (9:30 a.m.) is the set alarm. Smart alarm program 300 determines if the current time is of or after the set alarm time. In one scenario, the current time is 7:00 a.m. Smart alarm program 300 determines the time is not of or after the alarm time and so, returns to obtain the current time at a later interval. In another scenario, the current time is 9:30 a.m. Smart alarm program 300 determines the current time meets the alarm time. Smart alarm program 300 proceeds to play an alarm for Abel at 9:30 a.m. using alarm mod 105 on smart phone 204.

In another specific example to illustrate the functionality described above with respect to FIG. 2, a user of smart phone 204, Abel, inputs alarm settings and sleep cycle priorities into smart phone 204 using target UI 103. Abel's alarm settings and sleep cycle priorities are stored on database 220 as a user profile (user profile 221). Abel would like to be awoken at 8:00 a.m. Alternatively, if Abel is in deep sleep during the set alarm time, Abel would like to be awoken at 9:30 a.m. Abel inputs an alarm time for 8:00 a.m. and a backup alarm at 9:30 a.m. to play in the event Abel is experiencing deep sleep at the set alarm time. Smart alarm program 300 obtains the current time. Smart alarm program 300 identifies the set alarm time for 8:00 a.m. Smart alarm program 300 determines a guest is not present since no guest device is found by household sleep tracking monitor 214. Smart alarm program 300 proceeds to determine whether Abel has scheduled calendar events. Abel has no scheduled calendar events. Smart alarm program 300 determines no scheduled calendar events exist. Weather monitor 210 is used by smart alarm program 300 to identify the current weather conditions. Traffic monitor 216 obtains traffic-related data from multiple traffic data sources. Smart alarm program 300 determines there is safe travel conditions from data received from weather monitor 210 and traffic monitor

216. Smart alarm program 300 proceeds to determine whether the Abel's sleep cycle is prioritized. Abel set a backup alarm with instructions to use if he is experiencing deep sleep at the set alarm time. Smart alarm program 300 determines to use Abel's sleep cycle information. Smart alarm program 300 uses sleep cycle monitor 108 to monitor sleep patterns and determine the sleep cycle point of Abel. Sleep pattern information from Abel is obtained from wearable personal sleep trackers Abel is wearing. Smart alarm program 300 determines whether the sleep cycle point is an appropriate period for waking the user. In one scenario, Abel is experiencing deep sleep. Smart alarm program 300 cancels the set alarm (8:00 a.m.) and updates the alarm settings so that the backup alarm (9:30 a.m.) is the set alarm and returns to obtain the current time at a later interval. In another scenario, Abel is not experiencing deep sleep. Smart alarm program 300 determines if the current time is of or after the set alarm time. In one scenario, the current time is 7:00 a.m. Smart alarm program 300 determines the time is not of or after the alarm time and so, returns to obtain the current time at a later interval. In another scenario, the current time is 8:00 a.m. Smart alarm program 300 determines the current time meets the alarm time. Smart alarm program 300 proceeds to play an alarm for Abel at 8:00 a.m. using alarm mod 105 on smart phone 204.

Figure 3A:
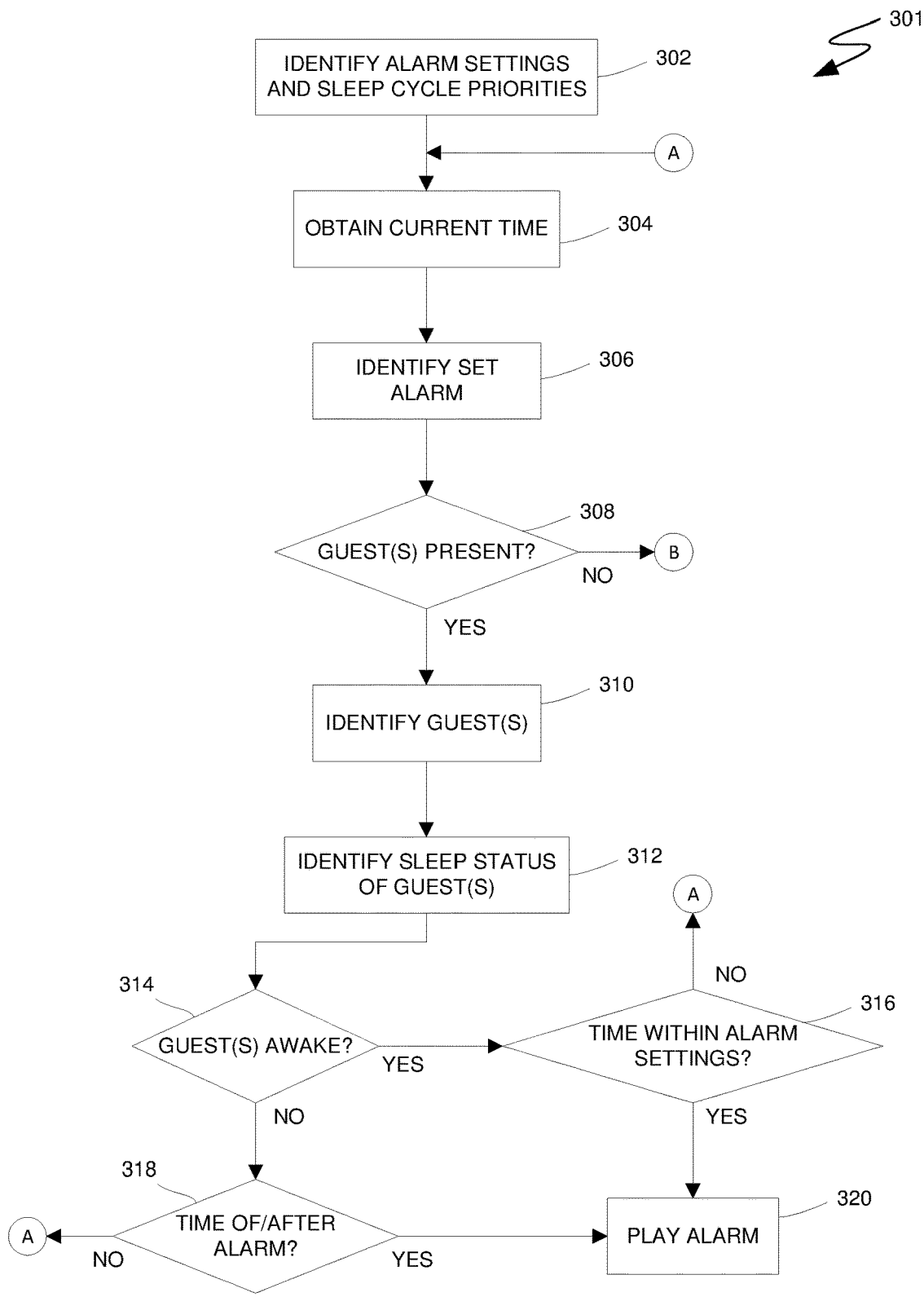
FIGS. 3A-3C are a flowchart depicting operations for playing an alarm based on a user's preferred parameters and sleep cycle, on a computing device within the computing environment of FIG. 1 and/or FIG. 2, in accordance with an embodiment of the present invention.
Figure 3B:
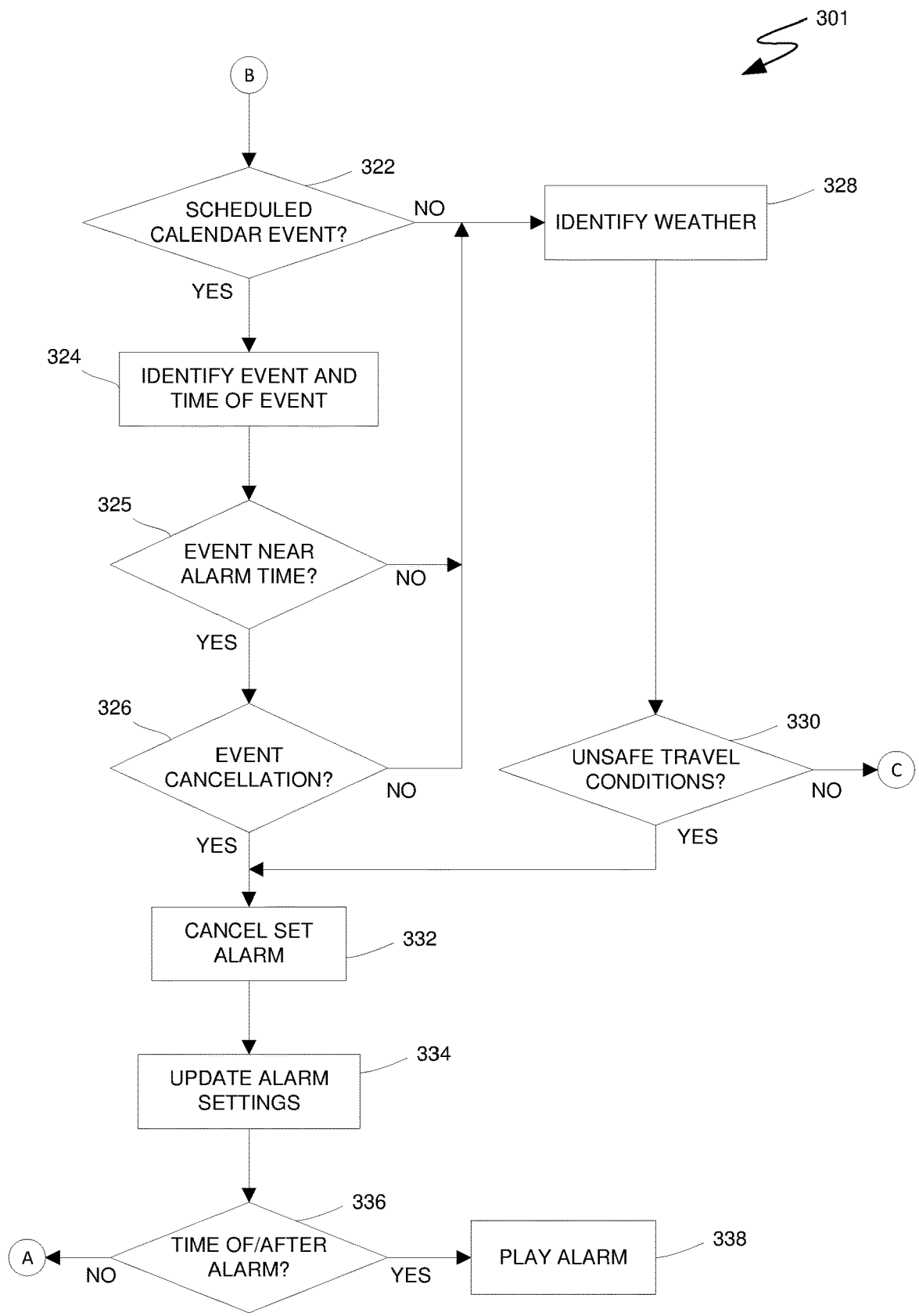
Figure 3C:
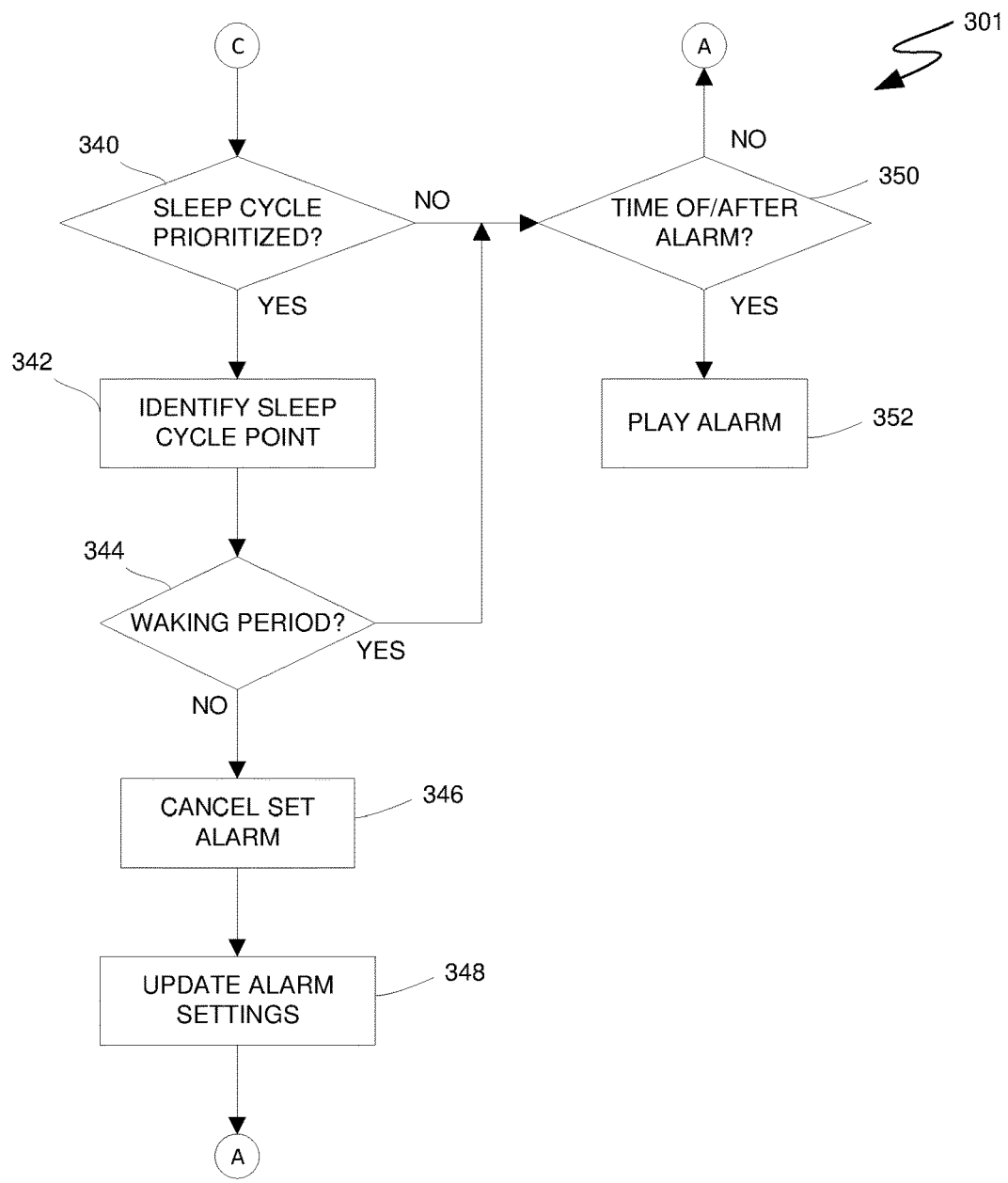

FIGS. 3A-3C are a flowchart depicting operations for playing an alarm based on a user's preferred parameters and/or sleep cycle, on a computing device within the computing environment of FIG. 1 and/or FIG. 2, in accordance with an embodiment of the present invention. For example, FIGS. 3A-3C are a flowchart depicting operations 301 of smart alarm program 300 on smart alarm server 112 within computing environment 100 and/or computing environment 200. In other examples, FIGS. 3A-3C are a flowchart depicting operations 301 of smart alarm program 300 on target device 104 (e.g., smart phone 204) within computing environment 100 and/or computing environment 200. In different embodiments, there are multiple variations of the order of the steps that may be applied. For example, on certain days, a certain order of steps is applied, while on other days, a different order of steps is applied based, at least in part, the conditions that apply with respect to smart alarm program 300 on the respective days.

Smart alarm program 300 identifies alarm settings and sleep cycle priorities for a user and stores the identified alarm settings and sleep cycle priorities in a database (step 302, e.g., database 220). In some embodiments, the alarm settings and sleep cycle priorities are stored on the database as a user profile (e.g. user profile 221). The user can input alarm settings and sleep cycle priorities into target device 104 of FIG. 1 via target UI 103. In some embodiments, the alarm settings and sleep cycle priorities may be accessed by the user and the user may edit the given information. For example, a user of smart alarm program 300 uses smart phone 204 of FIG. 2 to input the alarm settings and sleep cycle priorities. In another embodiment, the alarm settings and sleep cycle priorities are inputted directly from a third-party source, such as a user's parent or guardian, an employer, medical services, event coordinators, or guests of the user. Alarm settings are rules for when an alarm is played for the user. Alarm settings may be a specific set time (such as an alarm set for 8:30 a.m.) or may be within a range of times (such as an alarm set between 7:00 a.m. to 9:00 a.m.). Alarm settings may be specific to certain situations and preferences of a user. If guests are present at a user's home, the user may set a specific alarm time as well as a range of times to wake up in case a guest has woken up before the user has. For example, a user sets an alarm time for 8:00 a.m. and sets a range of times to play an alarm in the event a guest is awake (such as between 6:00 a.m. and 8:00 a.m.). Additionally, some embodiments have alarm settings that serve as a backup alarm time in the event of specific scenarios. In some embodiments, if a user is concerned about possible event cancellations or unsafe travel conditions, a user may set a specific alarm time as well as a backup alarm time. For example, a user sets an alarm time for 9:00 a.m. and sets a backup alarm time for 10:00 a.m. in the event of a meeting cancellation or unsafe travel conditions. In yet other embodiments, if a user has prioritized sleep cycle implementation, the user may set a specific alarm time and a backup alarm time if the user is experiencing deep sleep at the set alarm time. For example, a user sets an alarm time for 8:00 a.m. and sets a backup alarm time for 9:30 am, in the event the user is experiencing deep sleep at the 8:00 a.m. alarm time.

In some embodiments, the sleep cycle priorities identified in step 302 are rules to decide when to utilize sleep cycle information for a backup alarm. In other embodiments, sleep cycle prioritization are rules to decide if sleep cycle information should be utilized with respect to alarm settings. Based on user preferences, a user may set a backup alarm, so the user can wake up during the next period of light sleep, rather than waking up during a period of deep sleep. In some embodiments, sleep cycle prioritization may trump other parameter services. For example, a user may prioritize waking up during light sleep over waking up from a set alarm or a backup alarm in the case of an event cancellation. In other embodiments, sleep cycle information may be the lowest priority. For example, other parameter services and their respective alarm settings has higher priority to a user than waking up during light sleep. In yet other embodiments, any combination of priorities between the various parameter services described herein (e.g., weather, calendaring, household sleep tracking, and traffic) and sleep cycle information may be used. For example, certain parameter services and their respective alarm settings may be prioritized over sleep cycle information, while other parameter services and their respective alarm settings may be prioritized under sleep cycle information.

Smart alarm program 300 obtains the current time (step 304). In some embodiments, smart alarm program 300 obtains the current time from clock services found in a user's device, such as target device 104 of FIG. 1. The current time may be obtained periodically based on user preferences. For example, a user sets for the current time to be obtained once every second. Once a current time is obtained, smart alarm program 300 uses that time as the current time and proceeds until the current time is obtained again by smart alarm program 300. If a current time is obtained again by smart alarm program 300 (i.e., a subsequent iteration of step 304), the time obtained replaces the previously obtained time.

Smart alarm program 300 identifies the set alarm based on a user's alarm settings (step 306). The set alarm is the alarm time used by smart alarm program 300 to play an alarm for the user. For example, a user inputs an alarm time for 9:00 a.m. and a backup alarm time for 10:00 a.m. in the event of a meeting cancellation. Smart alarm program 300 identifies the set alarm as 9:00 a.m. If a set alarm is cancelled and the alarm settings are updated, the set alarm may be identified as a different alarm time in a subsequent iteration of step 306. Using the above example, in a subsequent iteration of step 306, smart alarm program 300 identifies the backup alarm time of 10:00 a.m. as the set alarm, after the previous set alarm is cancelled and the alarm settings are updated, as discussed further with respect to steps 332 and 334.

Having identified the set alarm, in the embodiment depicted in FIG. 3A, smart alarm program 300 determines whether guest(s) are present (decision step 308). Decision step 308 and the other steps of FIG. 3A-3C depict an embodiment where data from parameter sources are prioritized in the following order: household sleep tracking data, calendar data, weather data, traffic data, and sleep cycle data. However, smart alarm program 300 may be depicted as embodiments where data from parameter sources are prioritized in various other order. In some embodiments, smart alarm program 300 identifies whether guest devices, such as guest device 106 of FIG. 1, are present at the home of a user. Based off of whether guest devices are present, smart alarm program 300 determines guests are present. A user's device, such as target device 104, may communicate over a network, such as network 102, with guest devices by wireless local area network (WLAN) communication, near-field communication (NFC), radio-frequency identification (RFID), and/or Bluetooth communication. For example, a user's device communicates via Bluetooth with a guest's device, while the guest is staying at the user's home. Smart alarm program 300 identifies the guest is present based on the Bluetooth communication between the user's device and the guest's device. In other embodiments, a user identifies the presence of guests with smart alarm program 300 via a user interface, such as target UI 103 located on user's target device 104. In yet other embodiments, a guest identifies the presence of the guest with smart alarm program 300 via a user interface, such as guest UI 107 located on guest device 106.

For the case in which smart alarm program 300 determines guest(s) are present (step 308, "YES" branch), smart alarm program 300 proceeds to identify the guest(s) (step 310). In some embodiments, smart alarm program 300 identifies guests based on whether guest devices, such as guest device 106 of FIG. 1, are present at the home of a user. When guest devices are present, smart alarm program 300 identifies each specific guest. Smart alarm program 300 identifies the guest from information communicated over a network and received from the guest's device. In other embodiments, a user manually identifies a specific guest for smart alarm program 300 via a user interface, such as target UI 103 located on user's target device 104. In yet other embodiments, a guest manually identifies the guest for smart alarm program 300 via a user interface, such as guest UI 107 located on guest device 106.

Smart alarm program 300 identifies the sleep status of guest(s) present (step 312). In some embodiments, a parameter monitor, such as parameter monitor 110A of FIG. 1, specific to tracking household sleep patterns, such as household sleep tracking monitor 214 of FIG. 2, is used by smart alarm program 300 to determine the sleep status of guests. In some embodiments, household sleep tracking monitor 214 obtains household sleep tracking data from a guest device, such as guest device 106. In some embodiments, guest device 106 is one or more sleep cycle monitor devices that can monitor sleep patterns for members of a household or visitors of a household. In other embodiments, guest device 106 is a smart device, such as a smart phone, that can communicate with sleep cycle monitor devices. The sleep status of guests is the state of awakeness of guests. In one embodiment, there are two states of awakeness: awake or asleep. Sleep status information can be obtained from wearable PSG devices or wearable personal sleep trackers located on guests, as described herein. In other embodiments, a guest manually identifies the guest's sleep status for smart alarm program 300 via a user interface, such as guest UI 107 located on guest device 106. For example, a guest staying with a user wakes up before the user does. The guest, using the guest's device, can identify the sleep status of the guest, which in this case is "awake."

Having identified the sleep status of guest(s), smart alarm program 300 determines whether the guest(s) are awake (decision step 314). In one embodiment, there are two sleep statuses: awake or asleep. Using information identifying the sleep status of guests, smart alarm program 300 proceeds based on information on whether the guests are awake. In some embodiments, a sleep status of awake is determined when a guest is awake for a particular amount of time all at once. Certain individuals wake up from sleep but go right back to sleep soon after. In these cases, smart alarm program 300 would not proceed as though the guests are awake. For example, smart alarm program 300 can be configured so the sleep status of a guest is determined to be awake only when the guest is awake for longer than 10 minutes all at once. If the guest is awake for 5 minutes, but then goes back to sleep, smart alarm program 300 determines the guest is not awake. If the guest is awake for over 10 minutes, smart alarm program 300 determines the guest is awake.

For the case in which smart alarm program 300 determines the guest(s) are awake (step 314, "YES" branch), smart alarm program 300 proceeds to determine whether the obtained time is within alarm settings (decision step 316). Certain individuals wake up from sleep at all hours of the day for a number of reasons. A user may not want to be awakened when a guest is awake unless the guest is awake at specific hours of the day. Alarm settings may be specific to certain situations and preferences of a user. When guests are present at a user's home, the user may set a specific alarm time as well as a range of times to wake up in case a guest woke up before the user has. Smart alarm program 300 determines whether the obtained time from step 304 is within a range of times stipulated by a user. For example, a user sets a range of times as between 6:00 a.m. and 8:00 a.m. to play an alarm in the event a guest is awake. If a guest is awake at 5:00 am, smart alarm program 300 determines the obtained time is not within alarm settings. If a guest is awake at 7:00 am, smart alarm program 300 determines the obtained time is within alarm settings. In some embodiments, a range of times may not be set as alarm settings. In this case, any time a guest is awake, smart alarm program 300 determines the obtained time is within alarm settings.

For the case in which smart alarm program 300 determines the guest(s) are not awake (step 314, "NO" branch), smart alarm program 300 proceeds to determine whether the obtained time is of or after the set alarm time (decision step 318). Smart alarm program 300 determines whether the obtained time of step 304 is at or after the set alarm time identified in step 306. This is to determine whether it is time to play an alarm for a user. For example, if the set alarm time is 8:00 a.m. and the obtained time is 7:50 am, smart alarm program proceeds as though the obtained time is not of or after the set alarm time.

For the case in which smart alarm program 300 determines the obtained time is not within alarm settings (step 316, "NO" branch) or for the case in which smart alarm program 300 determines the time is not of or after the set alarm time (step 318, "NO" branch), smart alarm program 300 returns to step 304 to obtain the current time. In this case, smart alarm program 300 proceeds to return to step 304 to obtain the current time at a later time (i.e., a subsequent iteration of step 304). For the case in which smart alarm program 300 determines the obtained time is within alarm settings (step 316, "YES" branch) or for the case in which smart alarm program 300 determines the time is of or after the set alarm time (step 318, "YES" branch), smart alarm program 300 proceeds to play an alarm for the user (step 320). Smart alarm program 300 plays an alarm for the user if the set alarm time has been met or if the guests are awake and the obtained time is within alarm settings. In one example, a user sets an alarm time of 8:00 a.m. and a range of alarm times of 6:00 a.m. to 8:00 a.m. to be used if a guest is awake during that time. The guest remains asleep past 8:00 a.m. Smart alarm program 300 plays an alarm at 8:00 a.m. for the user, as the set alarm time has been met. In another example, a user sets an alarm time of 8:00 a.m. and a range of alarm times of 6:00 a.m. to 8:00 a.m. to be used if a guest is awake during that time. The guest wakes up at 7:00 a.m. Smart alarm program 300 plays an alarm at 7:00 a.m. for the user, as the obtained time (7:00 a.m.) is within the range of times of the alarm settings (6:00 a.m. to 8:00 a.m.). In some embodiments, the alarm is played from a user's device with alarm capabilities, such as from alarm mod 105 of target device 104 of FIG. 1. In some embodiments, the alarm played for the user consists of customizable sounds or music, or, in other embodiments, the alarm consists of vibration and/or displays of light.

For the case in which smart alarm program 300 determines guest(s) are not present (step 308, "NO" branch), smart alarm program 300 proceeds to determine whether a user has scheduled calendar events (decision step 322). Decision step 322 and the other steps of FIG. 3A-3C depict an embodiment where data from parameter sources are prioritized in the following order: household sleep tracking data, calendar data, weather data, traffic data, and sleep cycle data. However, smart alarm program 300 may be depicted as embodiments where data from parameter sources are prioritized in various other orders.

In some embodiments, a parameter monitor, such as parameter monitor 110B of FIG. 1, specific to tracking calendar events, such as calendaring monitor 212 of FIG. 2, is used by smart alarm program 300 to determine whether scheduled calendar events exist for the day of the set alarm time. A parameter monitor, such as calendaring monitor 212, obtains schedule and calendar-related data of a user from one or more calendar data sources. Calendaring monitor 212 is described above in greater detail with respect to FIG. 2.

For the case in which smart alarm program 300 determines a user has scheduled calendar events (step 322, "YES" branch), smart alarm program 300 proceeds to identify each event and the time of each event (step 324). In some embodiments, calendaring monitor 21 is used by smart alarm program 300 to determine the details of calendar events, such as what time the events occur, and whether or not calendar events are cancelled or rescheduled, as described herein.

Having identified an event and the time of the event, smart alarm program 300 determines whether the event is within a certain amount of time from the set alarm time (decision step 325). In some embodiments, a user may determine an amount of time an event's start time must be in proximity to the set alarm time. A user may be concerned about an event with a start time close after the set alarm time, while the user may not be as concerned about an event with a start time much later than the set alarm time. A user may configure smart alarm program 300, via a user interface, such as target UI 103 located on user's target device 104, to only consider events if the event starts within a certain amount of time after the set alarm time (i.e., a threshold amount of time). For example, a user configures smart alarm program 300 to determine if an identified event is to start within 2 hours (i.e., a 2 hour or 120-minute threshold) from the set alarm time. The user has a set alarm time of 9:00 a.m. Smart alarm program 300 identifies a calendar event scheduled to start at 12:30 p.m. Smart alarm program 300 determines the event does not start within 2 hours from the set alarm time since the event starts 3.5 hours after the set alarm time. In some embodiments, a rescheduled or delayed event is treated as, or is equivalent to, a cancelled event if the start time of the rescheduled event is outside of the threshold amount of time with respect to the set alarm time.

For the case in which smart alarm program 300 determines the event is near the set alarm time (step 325, "YES" branch), smart alarm program 300 determines whether there is a cancellation of the event (decision step 326). Calendaring monitor 212, for example, may receive notices of meeting cancellations, delays, and reschedules. For example, if a user links a work meeting calendar with calendaring monitor 212, smart alarm program 300 can determines if a scheduled calendar event listed in the work meeting calendar has been cancelled by querying calendaring monitor 212 for a current list of meetings and/or event notices (i.e., cancellation or scheduling notices) and comparing a received data to previously stored data and/or data previously obtained from calendaring monitor 212.

For the case in which smart alarm program 300 determines a user does not have scheduled calendar events (step 322, "NO" branch), for the case in which smart alarm program 300 determines an event is not within a certain amount of time from the seta alarm time (step 325, "NO" branch), or for the case in which smart alarm program 300 determines there is not a cancellation of an event (step 326, "NO" branch), smart alarm program 300 proceeds to identify the current weather conditions of the travel route of the user (step 328). In some embodiments, a parameter monitor, such as parameter monitor 110C of FIG. 1, specific to tracking weather events, such as weather monitor 210 of FIG. 2, is used by smart alarm program 300 to identify the current and/or predicted weather conditions (e.g., weather forecasts). Weather monitor 210 is described above in greater detail with respect to FIG. 2.

Having identified the current weather conditions, smart alarm program 300 determines whether there are unsafe travel conditions on the travel route of the user (decision step 330). In general, unsafe weather conditions are typical of unsafe travel conditions. A user, however, may configure what constitutes unsafe weather conditions for smart alarm program 300 via target UI 103 on the target device 104. For example, a user may configure any weather-related event that changes a travel time as unsafe weather conditions. Unsafe weather conditions may include snowfall, heavy rain, or tornadoes, as these weather events are typical of unsafe travel conditions.

In other embodiments, a parameter monitor, specific to tracking traffic events, such as traffic monitor 216 of FIG. 2, is used by smart alarm program 300 to identify unsafe traffic conditions on the travel route of the user in conjunction with or independent from weather monitor 210. Traffic monitor 216 is described above in greater detail with respect to FIG. 2.

For the case in which smart alarm program 300 determines there is a cancellation of an event (step 326, "YES" branch) or for the case in which smart alarm program 300 determines there are unsafe travel conditions (step 330, "YES" branch), smart alarm program 300 proceeds to cancel the set alarm time (step 332). The set alarm time identified in step 306 is cancelled in order for a backup alarm time to become the set alarm time when the alarm settings are updated. For example, a user sets an alarm at 8:00 a.m. and a backup alarm at 10:00 a.m. in case of an event cancellation. If an event at 9:00 a.m. is cancelled, smart alarm program 300 would proceed to cancel the alarm set for 8:00 a.m. In some embodiments, a user can designate an alarm that cannot be cancelled by smart alarm program 300. This alarm may be used as a failsafe alarm that can be used if no other backup alarm exists.

Smart alarm program 300 updates the alarm settings for the current day and stores the updated alarm settings in a database (step 334, e.g., database 220). In some embodiments, the updated alarm settings are stored on the database as a user profile (e.g. user profile 221). Additionally, in some embodiments, alarm settings comprise of a backup alarm time to be used as a set alarm time in the event the set alarm is cancelled. For example, a set alarm time is 9:00 a.m. and a backup alarm time is 10:00 a.m. If the set alarm time is cancelled, the backup alarm time of 10:00 a.m. becomes the set alarm time and is used as the alarm time to play an alarm for the user by smart alarm program 300.

Having updated the alarm settings, smart alarm program 300 determines whether the obtained time is of or after the set alarm time (decision step 336). Similar to decision step 318, smart alarm program 300 determines whether the obtained time of step 304 is at or after the set alarm time identified in step 306. This is to determine whether it is time to play an alarm for a user. For example, if the set alarm time is 8:00 a.m. and the obtained time is 7:50 am, smart alarm program proceeds as though the obtained time is not of or after the set alarm time.

For the case in which smart alarm program 300 determines the time is not of or after the set alarm time (step 336, "NO" branch), smart alarm program 300 returns to step 304 to obtain the current time. In this case, smart alarm program 300 proceeds to return to step 304 to obtain the current time at a later time (i.e., a subsequent iteration of step 304). For the case in which smart alarm program 300 determines the time is of or after the set alarm time (step 336, "YES" branch), smart alarm program 300 proceeds to play an alarm for the user (step 338). Similar to step 320, smart alarm program 300 plays an alarm for the user if the set alarm time has been met.

For the case in which smart alarm program 300 determines there are safe travel conditions (step 330, "NO" branch), smart alarm program 300 proceeds to determine whether the user's sleep cycle is prioritized (decision step 340). In some embodiments, sleep cycle prioritization are rules to decide when to utilize sleep cycle information for a backup alarm. In other embodiments, sleep cycle prioritization are rules to decide if sleep cycle information should be utilized with respect to alarm settings. Based on user preferences, a user may set a dynamic backup alarm, so the user can wake up during a period of light sleep, rather than waking up during a period of deep sleep. Smart alarm program 300 determines if the user's sleep cycle is prioritized from the alarm settings and sleep cycle priorities identified in step 302.

For the case in which smart alarm program 300 determines the user's sleep cycle is prioritized (step 340, "YES" branch), smart alarm program 300 proceeds to identify the point in the user's sleep cycle (step 342). In some embodiments, a sleep cycle monitor, such as sleep cycle monitor 108 of FIG. 1, is used by smart alarm program 300 to monitor sleep patterns and determine the sleep cycle point of the user. Sleep cycle monitor 108 is described above in greater detail with respect to FIGS. 1 and 2.

Having identified the point in the user's sleep cycle, smart alarm program 300 determines whether the sleep cycle point is an appropriate period for waking the user (decision step 344). Since the human body responds differently during stages associated with light sleep and stages associated with deep sleep, in some embodiments, only stages associated with light sleep are considered appropriate, by smart alarm program 300, for waking the user. Waking up during deep sleep tends to cause grogginess or disorientation. Waking up during the early stages of sleep, or "light sleep" tends to make people feel energetic and alert upon awakening. In other embodiments, all stages besides REM sleep are considered appropriate, by smart alarm program 300, for waking the user. The REM stage is the deepest stage of sleep. In some embodiments, a user may designate a range of times where smart alarm program 300 will only play an alarm during those times. For example, a user designates a range of times between 7:00 a.m. and 9:00 a.m. Smart alarm program 300 will only associate times between 7:00 a.m. and 9:00 a.m. as an appropriate period for waking the user. If the user is experiencing light sleep at 6:30 am, smart alarm program 300 would not play an alarm. Instead, iterations will follow until the user experiences a period of light sleep between 7:00 a.m. and 9:00 a.m. This assures that the user would only wake up during user-designated times.

For the case in which smart alarm program 300 determines the sleep cycle point is not an appropriate period for waking the user (step 344, "NO" branch), smart alarm program 300 proceeds to cancel the set alarm time (step 346). Similar to step 332, the set alarm time identified in step 306 is cancelled in order for a backup alarm time to become the set alarm time when the alarm settings are updated.

Smart alarm program 300 updates the alarm settings for the current day and stores the updated alarm settings in a database (step 348, e.g., database 220). Step 348 updates alarm settings similar to step 334. Having updated the alarm settings, smart alarm program 300 returns to step 304 to obtain the current time. In this case, smart alarm program 300 proceeds to return to step 304 to obtain the current time at a later time (i.e., a subsequent iteration of step 304). In some embodiments, smart alarm program 300 is configured to wake up the user during the user's next period of light sleep. In this case, the updated alarm settings reflect the time smart alarm program 300 calculates as the time when user will be experiencing light sleep.

For the case in which smart alarm program 300 determines the user's sleep cycle is not prioritized (step 340, "NO" branch) or for the case in which smart alarm program 300 determines the sleep cycle point is an appropriate period for waking the user (step 344, "YES" branch), smart alarm program 300 proceeds to determine whether the obtained time is of or after the set alarm time (decision step 350). Similar to decision steps 318 and 336, smart alarm program 300 determines whether the obtained time of step 304 is at or after the set alarm time identified in step 306. This is to determine whether it is time to play an alarm for a user. For example, if the set alarm time is 8:00 a.m. and the obtained time is 7:50 am, smart alarm program proceeds as though the obtained time is not of or after the set alarm time.

For the case in which smart alarm program 300 determines the time is not of or after the set alarm time (step 350, "NO" branch), smart alarm program 300 returns to step 304 to obtain the current time. In this case, smart alarm program 300 proceeds to return to step 304 to obtain the current time at a later time (i.e., a subsequent iteration of step 304). For the case in which smart alarm program 300 determines the time is of or after the set alarm time (step 350, "YES"

branch), smart alarm program 300 proceeds to play an alarm for the user (step 352). Similar to steps 320 and 338, smart alarm program 300 plays an alarm for the user if the set alarm time has been met.

Figure 4:
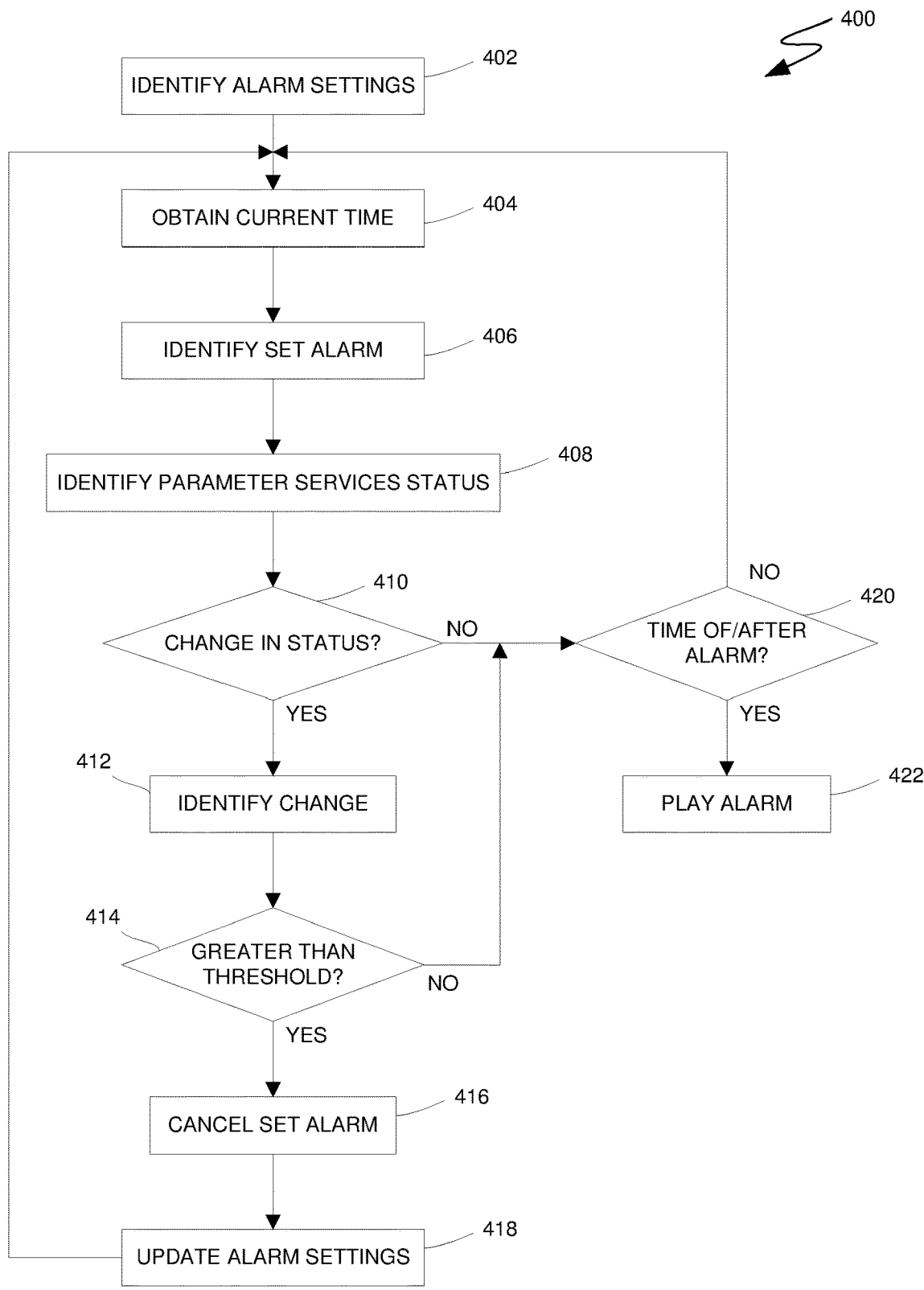
FIG. 4 is a flowchart depicting operations for playing an alarm based on a user's preferred parameters and sleep cycle, on a computing device within the computing environment of FIG. 1 and/or FIG. 2, in accordance with an embodiment of the present invention.

FIG. 4 is a flowchart depicting operations for playing an alarm based on a user's preferred parameters and sleep cycle, on a computing device within the computing environment of FIG. 1 and/or FIG. 2, in accordance with an embodiment of the present invention. For example, FIG. 4 is a flowchart depicting operations 400 of smart alarm program 300 on smart alarm server 112 within computing environment 100 and/or computing environment 200. In other examples, FIG. 4 is a flowchart depicting operations 400 of smart alarm program 300 on target device 104 (e.g., smart phone 204) within computing environment 100 and/or computing environment 200.

Smart alarm program 300 identifies alarm settings and stores the identified alarm settings in a database (step 402, e.g., database 220). In some embodiments, the alarm settings are stored on the database as a user profile (e.g. user profile 221). The user can input alarm settings into target device 104 of FIG. 1 via target UI 103. Step 402 is similar to step 302 of FIG. 3 and is described above in greater detail.

Smart alarm program 300 obtains the current time (step 404). Step 404 is similar to step 304 of FIG. 3 and is described above in greater detail. If a current time is obtained again by smart alarm program 300 (i.e., a subsequent iteration of step 404), the time obtained replaces the previous obtained time.

Smart alarm program 300 identifies the set alarm based on a user's alarm settings (step 406). Step 404 is similar to step 304 of FIG. 3 and is described above in greater detail. If a set alarm is cancelled and the alarm settings are updated, the set alarm may be identified as a different alarm time in a subsequent iteration of step 406.

Smart alarm program 300 identifies the statuses of parameter services and stores the statuses in a database (step 408, e.g., database 220). In some embodiments, parameter monitors, such as parameter monitors 110 of FIG. 1, monitor information from external parameter data sources. Parameter monitors receive data from external parameter data sources and monitors the data, based on user configured preferences, for the statuses of the data. A user may configure parameter monitors to monitor data at certain intervals (i.e. constantly, every 15 minutes, hourly, etc.). In some embodiments, a parameter service status is a descriptor of the data tracked by the parameter service. For example, a parameter monitor, specific to tracking weather, such as weather monitor 210 of FIG. 2, reports to smart program 300 that the status of weather is "sunny." As a parameter monitor monitors data from an external parameter data sources, a subsequent iteration (i.e. a subsequent iteration of step 408) may result in a different status. Using the previous example, a subsequent iteration results in the parameter monitor reporting to smart program 300 that the status of weather is "raining."

Having identified the statuses of parameter services, smart alarm program 300 determines whether a change in the statuses of the parameter services has occurred (decision step 410). In some embodiments, smart alarm program 300 compares the identified statuses from step 408 with statuses from a previous iteration of step 408. A user may configure what constitutes a change in data. In some embodiments, any status different from the status from a previous iteration as a change in status. In other embodiments, any status that may result in a change in travel time may constitute a change in data. For example, a previous iteration results in a status of "sunny" from a parameter monitor specific to tracking weather, such as weather monitor 210 of FIG. 2. The current status reported by the parameter monitor is "cloudy." A user configures any weather-related event that changes a travel time as a weather change. Smart alarm program determines there is no change in the status, as weather changing from "sunny" to "cloudy" would likely not alter travel time. In another example, a previous iteration results in a status of "sunny" from a parameter monitor specific to tracking weather, such as weather monitor 210 of FIG. 2. The current status reported by the parameter monitor is "snowing." A user configures any weather-related event that changes a travel time as a weather change. Smart alarm program determines there is a change in the status, as weather changing from "sunny" to "snowing" would likely alter travel time. Each status may correspond to a severity rating, detailed in the following step.

For the case in which smart alarm program 300 determines there is a change in the statuses of the parameter services (step 410, "YES" branch), smart alarm program 300 identifies the change (step 412). Smart alarm program 300 obtains information on the change in statuses. In some embodiments, smart alarm program 300 obtains information on the severity of the statuses of the parameter services in relation to its detrimental effect on travel time. In this case, each status may correspond to a severity rating, based on the likelihood of causing a difference in travel time. A user may input severity ratings of each status into target device 104 of FIG. 1 via target UI 103. Similarly, a parameter monitor collecting data for a parameter status may assign a severity rating to the parameter status. These severity ratings may be stored in a database, such as database 220, along with the statuses of parameter services. In an example, smart alarm program 300 identifies the severity of the status "snowing" as low, because, although it is snowing, it is considered light snow based on information collected from weather monitor 210. Weather monitor 210 assigns a low severity rating as light snow would likely not detrimentally affect travel time. In another example, smart alarm program 300 identifies the severity of the status "snowing" as high, because, it is considered heavy snow based on information collected from weather monitor 210. Weather monitor 210 assigns a high severity rating as heavy snow would likely not detrimentally affect travel time.

Having identified the change in status in status of the parameter services, smart alarm program 300 determines whether the change is greater than a threshold (decision step 414). In some embodiments, the severity ratings of the statuses of the parameter services are compared to a threshold. The threshold is the difference in ratings of the identified status and the status of the previous iteration (i.e. a previous iteration of step 408). A threshold that would result in a cancelled set alarm time would result be a difference between a low severity rating and a high severity rating. A user can input the thresholds for each status into target device 104 of FIG. 1 via target UI 103. These thresholds may be stored in a database, such as database 220, along with the statuses of parameter services and the severity ratings. In an example, a user sets a threshold. In a previous iteration, smart alarm program 300 identifies the status to be "sunny." In the current iteration, smart alarm program 300 identifies the status to be "light snow." Smart alarm program 300 determines the change is not greater than a threshold since both "sunny" and "light snow" correspond to low severity ratings. Minor changes in statuses do not result in a difference greater than the listed threshold. In another example, a user sets a threshold. In a previous iteration, smart alarm program 300 identifies the status to be "light snow." In the current iteration, smart alarm program 300 identifies the status to be "heavy snow." Smart alarm program 300 determines the change is greater than a threshold since "light snow" correspond to a low severity rating, while "heavy snow" correspond to a high severity rating. Major changes in statuses result in a difference greater than the listed threshold. In other embodiments, smart alarm program 300 determines whether the change is greater than a time threshold. The time threshold is an amount of time the user designates. Smart alarm program 300 calculates the amount of time delayed from the identified parameter services statuses. For example, smart alarm program 300 calculates snow will delay travel time by 40 minutes. A user designates a time threshold of 10 minutes. If travel time is delayed for longer than 10 minutes, the user would like to use a backup alarm. In this example, smart alarm program 300 proceeds to determine the time is greater than the time threshold ("YES branch). If smart alarm program 300 calculated that the snow will delay travel time by 5 minutes, smart alarm program 300 would proceed with the "NO" branch.

For the case in which smart alarm program 300 determines the change to be greater than a threshold (step 414, "YES" branch), smart alarm program 300 proceeds to cancel the set alarm time (step 416). The set alarm time identified in step 406 is cancelled in order for a backup alarm time to become the set alarm time when the alarm settings are updated. For example, a user sets an alarm at 8:00 a.m. The weather in the area is reported to be heavy snow. A user sets a threshold. A previous iteration of the status is "sunny." The current reported status is "heavy snow." The change between the iterations of statuses exceeds the threshold. Smart alarm program 300 proceeds to cancel the alarm time of 8:00 a.m.

Smart alarm program 300 updates the alarm settings for the current day and stores the updated alarm settings in a database (step 418, e.g., database 220). In some embodiments, the updated alarm settings are stored on the database as a user profile (e.g. user profile 221). Additionally, in some embodiments, alarm settings comprise of a backup alarm time to be used as a set alarm time in the event the set alarm is cancelled. For example, a set alarm time is 9:00 a.m. and a backup alarm time is 10:00 a.m. If the set alarm time is cancelled, the backup alarm time of 10:00 a.m. becomes the set alarm time and is used as the alarm time to play an alarm for the user by smart alarm program 300. In other embodiments, no backup alarm time is used with the set alarm time. In this case, the set alarm time is adjusted based on the calculated travel time given the travel conditions. The alarm time is adjusted to ensure the user arrives at a location as expected if the user woke up during the set alarm time during normal driving conditions. The adjusted alarm time is identified in a subsequent iteration as the set alarm time in a subsequent iteration of step 406. For example, snow fall cause the travel time for a user to arrive at the user's workplace to increase by 20 minutes. The user had previously set the alarm time to be 9:00 a.m. Smart alarm program 300 updates the alarm settings by adjusting the set alarm time to occur 20 minutes before the set alarm time. The updated set alarm time is now 8:40 am, so that the user is allowed 20 extra minutes. Smart alarm program 300 returns to step 404 to obtain the current time. In this case, smart alarm program 300 proceeds to return to step 404 to obtain the current time at a later time (i.e., a subsequent iteration of step 404). In some embodiments, due to a frequency of iterations, step 418 may occur after step 420.

For the case in which smart alarm program 300 determines there is not a significant change in the statuses of the parameter services (step 410, "NO" branch) and for the case in which smart alarm program 300 determines the change to be not greater than a threshold (step 414, "NO" branch), smart alarm program 300 proceeds to determine whether the obtained time is of or after the set alarm time (decision step 420). Smart alarm program 300 determines whether the obtained time of step 404 is at or after the set alarm time identified in step 406. This is to determine whether it is time to play an alarm for a user. For example, if the set alarm time is 8:00 a.m. and the obtained time is 7:50 am, smart alarm program proceeds as though the obtained time is not of or after the set alarm time.

For the case in which smart alarm program 300 determines the time is not of or after the set alarm time (step 420, "NO" branch), smart alarm program 300 returns to step 404 to obtain the current time. In this case, smart alarm program 300 proceeds to return to step 404 to obtain the current time at a later time (i.e., a subsequent iteration of step 404). For the case in which smart alarm program 300 determines the time is of or after the set alarm time (step 420, "YES" branch), smart alarm program 300 proceeds to play an alarm for the user (step 422). Similar to steps 320, 338, and 352 of FIG. 3, smart alarm program 300 plays an alarm for the user if the set alarm time has been met.

Figure 5:
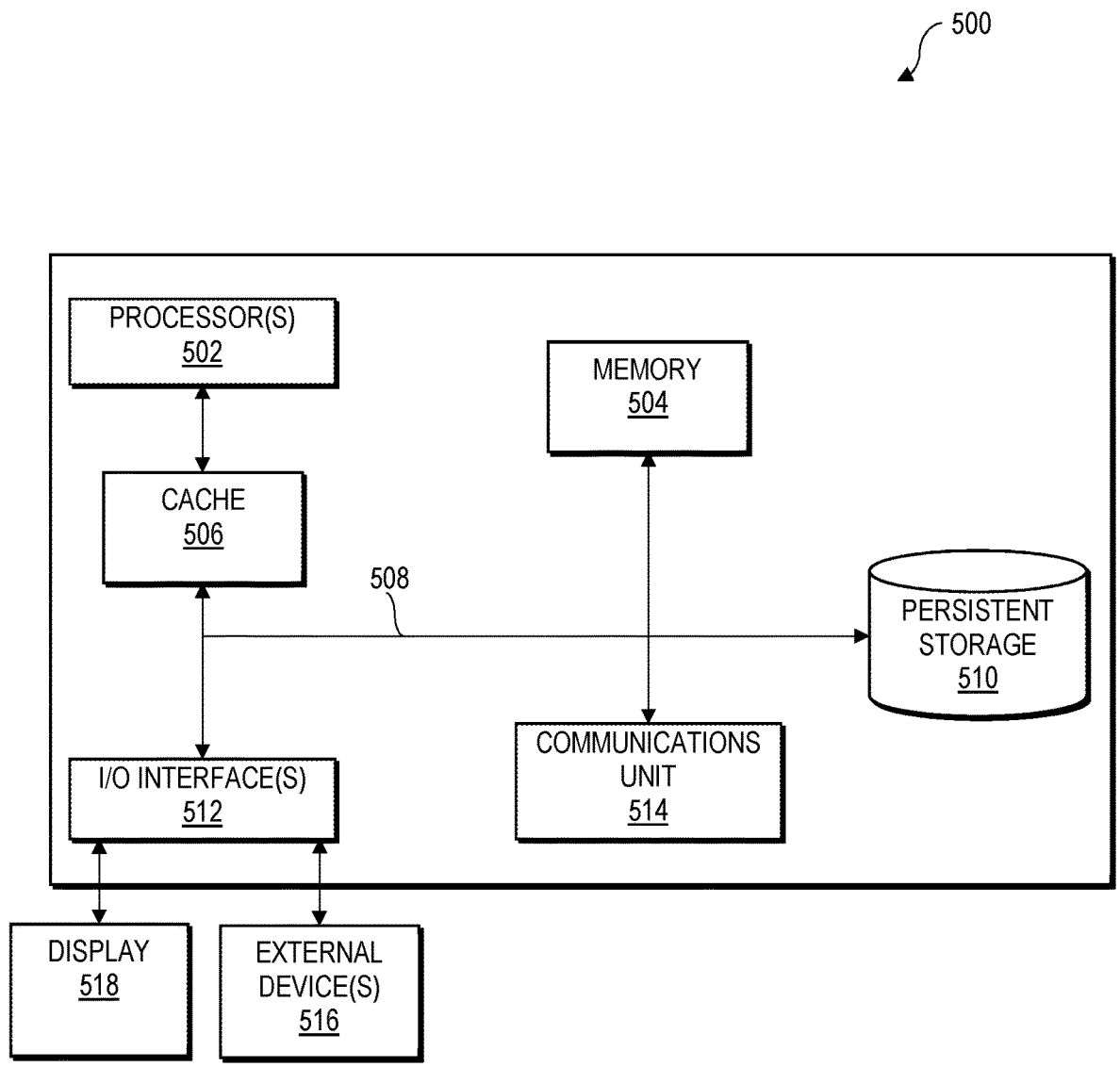
FIG. 5 is a block diagram of components of a computing device executing operations for playing an alarm based on a user's preferred parameters and sleep cycle, in accordance with an embodiment of the present invention.

FIG. 5 is a block diagram of components of a computing device, generally designated 500, in accordance with an embodiment of the present invention. In one embodiment, computing system 500 is representative of smart alarm server 112 within computing environment 100 and/or computing environment 200, in which case smart alarm server 112 includes smart alarm program 300.

It should be appreciated that FIG. 5 provides only an illustration of one implementation and does not imply any limitations with regard to the environments in which different embodiments may be implemented. Many modifications to the depicted environment may be made.

Computing system 500 includes processor(s) 502, cache 506, memory 504, persistent storage 510, input/output (I/O) interface(s) 512, communications unit 514, and communications fabric 508. Communications fabric 508 provides communications between cache 506, memory 504, persistent storage 510, communications unit 514, and input/output (I/O) interface(s) 512. Communications fabric 508 can be implemented with any architecture designed for passing data and/or control information between processors (such as microprocessors, communications, and network processors, etc.), system memory, peripheral devices, and any other hardware components within a system. For example, communications fabric 508 can be implemented with one or more buses or a crossbar switch.

Memory 504 and persistent storage 510 are computer readable storage media. In this embodiment, memory 504 includes random access memory (RAM). In general, memory 504 can include any suitable volatile or non-volatile computer readable storage media. Cache 506 is a fast memory that enhances the performance of processor(s) 502 by holding recently accessed data, and data near recently accessed data, from memory 504.

Program instructions and data used to practice embodiments of the present invention may be stored in persistent storage 510 and in memory 504 for execution by one or more of the respective processor(s) 502 via cache 506. In an embodiment, persistent storage 510 includes a magnetic hard disk drive. Alternatively, or in addition to a magnetic hard disk drive, persistent storage 510 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 510 may also be removable. For example, a removable hard drive may be used for persistent storage 510. Other examples include optical and magnetic disks, thumb drives, and smart cards that are inserted into a drive for transfer onto another computer readable storage medium that is also part of persistent storage 510.

Communications unit 514, in these examples, provides for communications with other data processing systems or devices. In these examples, communications unit 514 includes one or more network interface cards. Communications unit 514 may provide communications through the use of either or both physical and wireless communications links. Program instructions and data used to practice embodiments of the present invention may be downloaded to persistent storage 510 through communications unit 514.

I/O interface(s) 512 allows for input and output of data with other devices that may be connected to computer system 500. For example, I/O interface(s) 512 may provide a connection to external device(s) 516 such as a keyboard, keypad, a touch screen, and/or some other suitable input device. External device(s) 516 can also include portable computer readable storage media such as, for example, thumb drives, portable optical or magnetic disks, and memory cards. Software and data used to practice embodiments of the present invention can be stored on such portable computer readable storage media and can be loaded onto persistent storage 510 via I/O interface(s) 512. I/O interface(s) 512 also connect to display 518.

Display 518 provides a mechanism to display or present data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, a list of alternatives such as "at least one of A, B, and C" should be interpreted to mean "at least one A, at least one B, at least one C, or any combination of A, B, and C."

Additionally, the phrase "based on" should be interpreted to mean "based, at least in part, on."

The term "exemplary" means of or relating to an example and should not be construed to indicate that any particular embodiment is preferred relative to any other embodiment.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
    identifying a first range of alarm times to play a first alarm in a set of alarm settings;
    monitoring a user for a sleep status;
    determining the sleep status to be an awake status at a first time;
    determining whether the first time is within the first range of alarm times; and
    responsive to determining the first time is within the first range of alarm times, playing the first alarm.

2. The method of claim 1, wherein monitoring a user includes monitoring body functions, movement, and activity of the user to determine the sleep status.

3. The method of claim 1, further comprising:
    responsive to playing the first alarm, identifying a scheduled event on a calendar designated by the user, the scheduled event including a start time and an end time;
    identifying a second alarm time in the set of alarm settings;
    determining the second alarm time is within a threshold amount of time before the start time;
    responsive to determining the second alarm time is within a threshold amount of time before the start time, playing a second alarm at the second alarm time.

4. The method of claim 3, further comprising:
    determining the calendar event is cancelled according to social media calendar designated by the user;
    cancelling the second alarm time from the set of alarm settings; and
    updating the set of alarm settings to include a backup alarm time.

5. The method of claim 1, wherein:
    playing the first alarm is conditioned upon road conditions being safe for travel along a travel route, and
    the travel route is specified within the set of alarm settings; and
    further comprising:
    responsive to determining the road conditions are not safe, cancelling the first alarm; and
    updating the set of alarm settings to include a backup alarm time.

6. The method of claim 5, wherein:
    the backup alarm time is based on a prioritized sleep cycle; and
    further comprising:
    identifying a sleep cycle status, wherein periods of light sleep and periods of deep sleep comprise a sleep cycle;
    responsive to the sleep cycle status being a period of deep sleep setting the backup alarm time according to a pre-defined deep sleep period.

7. The method of claim 6, wherein identifying the sleep cycle status includes:
    monitoring body functions, movement, and activity of the user to determine the sleep cycle status.

8. A computer program product comprising a computer readable storage medium having a set of instructions stored therein which, when executed by a processor, causes the processor to selectively activate alarms according to a set of alarm settings by:
    identifying a first range of alarm times to play a first alarm in a set of alarm settings;
    monitoring a user for a sleep status;
    determining the sleep status to be an awake status at a first time;
    determining whether the first time is within the first range of alarm times; and
    responsive to determining the first time is within the first range of alarm times, playing the first alarm.

9. The computer program product of claim 8, wherein monitoring a user includes monitoring body functions, movement, and activity of the user to determine the sleep status.

10. The computer program product of claim 8, further causing the processor to selectively activate alarms according to a set of alarm settings by:
    responsive to playing the first alarm, identifying a scheduled event on a calendar designated by the user, the scheduled event including a start time and an end time;
    identifying a second alarm time in the set of alarm settings;

determining the second alarm time is within a threshold amount of time before the start time;

responsive to determining the second alarm time is within a threshold amount of time before the start time, playing a second alarm at the second alarm time.

11. The computer program product of claim 10, further causing the processor to selectively activate alarms according to a set of alarm settings by:

determining the calendar event is cancelled according to social media calendar designated by the user;

cancelling the second alarm time from the set of alarm settings; and updating the set of alarm settings to include a backup alarm time.

12. The computer program product of claim 8, wherein:

playing the first alarm is conditioned upon road conditions being safe for travel along a travel route, and the travel route is specified within the set of alarm settings; and further causing the processor to selectively activate alarms according to a set of alarm settings by:

responsive to determining the road conditions are not safe, cancelling the first alarm; and updating the set of alarm settings to include a backup alarm time.

13. The computer program product of claim 12, wherein:

the backup alarm time is based on a prioritized sleep cycle; and further causing the processor to selectively activate alarms according to a set of alarm settings by:

identifying a sleep cycle status, wherein periods of light sleep and periods of deep sleep comprise a sleep cycle;

responsive to the sleep cycle status being a period of deep sleep setting the backup alarm time according to a pre-defined deep sleep period.

14. The computer program product of claim 13, wherein identifying the sleep cycle status includes:

monitoring body functions, movement, and activity of the user to determine the sleep cycle status.

15. A computer system comprising:

a processor(s) set; and a computer readable storage medium having program instructions stored therein;

wherein:

the processor set executes the program instructions that cause the processor set to selectively activate alarms according to a set of alarm settings by:

identifying a first range of alarm times to play a first alarm in a set of alarm settings;

monitoring a user for a sleep status;

determining the sleep status to be an awake status at a first time;

determining whether the first time is within the first range of alarm times; and responsive to determining the first time is within the first range of alarm times, playing the first alarm.

16. The computer system of claim 15, wherein monitoring a user includes monitoring body functions, movement, and activity of the user to determine the sleep status.

17. The computer system of claim 15, further causing the processor to selectively activate alarms according to a set of alarm settings by:

responsive to playing the first alarm, identifying a scheduled event on a calendar designated by the user, the scheduled event including a start time and an end time;

identifying a second alarm time in the set of alarm settings;

determining the second alarm time is within a threshold amount of time before the start time;

responsive to determining the second alarm time is within a threshold amount of time before the start time, playing a second alarm at the second alarm time.

18. The computer system of claim 17, further causing the processor to selectively activate alarms according to a set of alarm settings by:

determining the calendar event is cancelled according to social media calendar designated by the user;

cancelling the second alarm time from the set of alarm settings; and updating the set of alarm settings to include a backup alarm time.

19. The computer system of claim 15, wherein:

playing the first alarm is conditioned upon road conditions being safe for travel along a travel route, and the travel route is specified within the set of alarm settings; and further causing the processor to selectively activate alarms according to a set of alarm settings by:

responsive to determining the road conditions are not safe, cancelling the first alarm; and updating the set of alarm settings to include a backup alarm time.

20. The computer system of claim 19, wherein:

the backup alarm time is based on a prioritized sleep cycle; and further causing the processor to selectively activate alarms according to a set of alarm settings by:

identifying a sleep cycle status, wherein periods of light sleep and periods of deep sleep comprise a sleep cycle;

responsive to the sleep cycle status being a period of deep sleep setting the backup alarm time according to a pre-defined deep sleep period.

\* \* \* \* \*